US012760258B2

(12) United States Patent
Zhou et al.

(10) Patent No.: US 12,760,258 B2
(45) Date of Patent: Oct. 13, 2026

(54) CELL CULTURE PROCESS BY INTENSIFIED PERFUSION WITH CONTINUOUS HARVEST AND WITHOUT CELL BLEEDING

(71) Applicant: WUXI BIOLOGICS IRELAND LIMITED, Dundalk (IE)

(72) Inventors: Weichang Zhou, Shanghai (CN); Hang Zhou, Shanghai (CN); Mingyue Fang, Shanghai (CN); Siyuan Tang, Shanghai (CN)

(73) Assignee: WUXI BIOLOGICS IRELAND LIMITED, Dundalk (IE)

( * ) Notice: Subject to any disclaimer, the term of this patent is extended or adjusted under 35 U.S.C. 154(b) by 1005 days.

(21) Appl. No.: 17/289,332

(22) PCT Filed: Sep. 29, 2019

(86) PCT No.: PCT/CN2019/108921

§ 371 (c)(1),
(2) Date: Apr. 28, 2021

(87) PCT Pub. No.: WO2020/088180

PCT Pub. Date: May 7, 2020

(65) Prior Publication Data

US 2022/0364034 A1 Nov. 17, 2022

(30) Foreign Application Priority Data

Nov. 2, 2018 (WO) ................ PCT/CN2018/113776
Jun. 4, 2019 (WO) ................ PCT/CN2019/089993

(51) Int. Cl.
*C12M 1/00* (2006.01)
*C12M 1/26* (2006.01)
*C12N 5/00* (2006.01)
*C12P 21/00* (2006.01)

(52) U.S. Cl.
CPC ............ *C12M 29/10* (2013.01); *C12M 29/06* (2013.01); *C12M 33/14* (2013.01); *C12N 5/00* (2013.01); *C12P 21/00* (2013.01)

(58) Field of Classification Search
None
See application file for complete search history.

(56) References Cited

U.S. PATENT DOCUMENTS 5,149,792 A 9/1992 Thomason
5,272,064 A 12/1993 Thomason
6,090,382 A 7/2000 Salfeld et al.
6,235,883 B1 5/2001 Jakobovits et al.
6,544,424 B1 4/2003 Shevitz
7,070,959 B1 7/2006 Papadopoulos et al.
7,294,484 B2 11/2007 Drapeau et al.
7,300,773 B2 11/2007 Drapeau et al.
7,335,491 B2 2/2008 Drapeau et al.
8,129,145 B2 3/2012 Lasko et al.
8,232,075 B2 7/2012 Luan et al.
8,440,458 B2 5/2013 Zijlstra et al.
8,580,554 B2 11/2013 Grillberger et al.
8,945,867 B2 2/2015 Ogawa et al.
9,469,865 B2 10/2016 Zijlstra et al.
9,650,612 B2 5/2017 Grillberger et al.
9,670,520 B2 6/2017 Zijlstra et al.
9,822,388 B2 11/2017 Wu et al.
10,138,290 B2 11/2018 Robin
10,167,492 B2 1/2019 Leiske et al.
2009/0042253 A1 2/2009 Hiller
2011/0256624 A1 10/2011 Jenne et al.
2015/0158907 A1 6/2015 Zhou et al.
2016/0298072 A1 10/2016 Laustsen
2017/0114381 A1 4/2017 Goudar et al.
2017/0166942 A1 6/2017 Gupta et al.
2017/0204446 A1* 7/2017 Cattaneo ............ B01D 15/3809
2018/0312802 A1 11/2018 Bielser et al.
2019/0169559 A1 6/2019 Coffman et al.

FOREIGN PATENT DOCUMENTS

CN 101048511 B 7/2012
CN 101061231 B 9/2012
CN 103305417 A 9/2013
CN 104878064 A 9/2015
CN 105722967 A 6/2016
CN 102827905 B 8/2016
CN 106687575 A 5/2017
CN 106987559 A 7/2017
CN 107109455 A 8/2017
CN 107190034 A 9/2017
CN 103827292 B 1/2018
CN 108504562 A 9/2018
CN 109072154 A 12/2018
EP 1 781 802 B1 10/2009
EP 1 992 697 B1 3/2010
EP 2 634 242 A1 9/2013
EP 2 041 270 B1 11/2013
EP 2 078 071 B1 3/2015
EP 2 625 262 B1 9/2015
(Continued)

OTHER PUBLICATIONS

Xu. "Bioreactor Productivity and Media Cost Comparison for Different Intensified Cell Culture Processes". 2017. (Year: 2017).*
Bielser J. M. et al. "Perfusion mammalian cell culture for recombinant protein manufacturing—A critical review" *Biotechnology Advances*, vol. 36, May 5, 2018 (May 5, 2018), ISSN: 0734-9750, pp. 1328-1340.
International Search Report, issued in PCT/CN2019/108921, dated Jan. 9, 2020 (seven pages).
Written Opinion of the International Searching Authority for International Application No. PCT/CN2019/108921 (six pages), 2020.
Xu S. et al. "Bioreactor Productivity and Media Cost Comparison for Different Intensified Cell Culture Processes," *Biotechnology Progress*, vol. 33, No. 4, pp. 867-878 (2017).
Yan X. et al. "Procedure and Application of Animal Cell Perfusion Culture System," *Progress in Veterinary Medicine*, vol. 35, No. 4, pp. 125-128 (2014).
(Continued)

*Primary Examiner* — Laura Schuberg
(74) *Attorney, Agent, or Firm* — James S. Keddie; Bozicevic, Field & Francis LLP

(57) ABSTRACT

Provided are a method and a system for culturing cells and harvesting biologics. More particularly process for cell culture by intensified perfusion with continuous harvest and without cell bleeding is provided.

14 Claims, 13 Drawing Sheets

(56) References Cited

FOREIGN PATENT DOCUMENTS

| | | | |
|---|---|---|---|
| EP | 2 041 259 | B1 | 10/2015 |
| EP | 2 343 362 | B1 | 3/2016 |
| EP | 2 726 600 | B1 | 2/2017 |
| EP | 1 789 571 | B1 | 4/2017 |
| EP | 2 634 250 | B1 | 4/2017 |
| EP | 2 634 243 | B1 | 9/2017 |
| EP | 2 188 371 | B1 | 12/2017 |
| EP | 2 970 874 | B1 | 9/2018 |
| EP | 3 152 317 | B1 | 1/2019 |
| JP | H0265778 | A | 3/1990 |
| JP | 2017-502666 | A | 1/2017 |
| JP | 2018-521664 | A | 8/2018 |
| WO | WO 2008/131374 | A1 | 10/2008 |
| WO | WO 2009/023562 | A2 | 2/2009 |
| WO | WO 2015/102528 | A1 | 7/2015 |
| WO | WO 2017/082990 | A1 | 5/2017 |
| WO | WO 2008/006494 | A1 | 1/2018 |
| WO | WO 2018/116198 | A1 | 6/2018 |
| WO | WO 2018/178063 | A1 | 10/2018 |
| WO | WO 2018/178069 | A1 | 10/2018 |
| WO | WO 2019/118426 | A1 | 6/2019 |

OTHER PUBLICATIONS

Office Action dated Apr. 10, 2023, received in Korean Pat. Application No. 10-2021-7015264, dated Apr. 10, 2023 (9 pages).

English Translation of Office Action dated Apr. 10, 2023, received in Korean Pat. Application No. 10-2021-7015264, dated Apr. 10, 2023 (10 pages).

S. Xu et al., "Bioreactor Productivity and Media Cost Comparison for Different Intensified Cell Culture Processes," *American Institute of Chemical Engineers*, 2015, pp. 867-878.

H. Kaufmann et al., "Influence of Low Temperature on Productivity, Proteome and Protein Phosphorylation of CHO Cells", *Biotechnology and Bioengineering*, vol. 63, No. 5, Jun. 5, 1999, pp. 573-582.

K. Furukawa et al., "Effect of culture temperature on a recombinant CHO cell line producing C-terminal α-amidating enzyme", *Cytotechnology*, 26, 1998, pp. 153-164.

H. Lin et al., "Principles and Approach to Developing Mammalian Cell Culture Media for High Cell Density Perfusion Process Leveraging Established Fed-Batch Media," *American Institute of Chemical Engineers*, 2017, pp. 891-901.

Kumar, N., et al., "Proliferation control strategies to improve productivity and survival during CHO based production culture", *Cytotechnology*, 53, pp. 33-46, Mar. 1, 2007 (Mar. 1, 2007).

Clincke, M.-F., et al., "Very High Density of Chinese Hamster Ovary Cells in Perfusion by Alternating Tangential Flow or Tangential Flow Filtration in WAVE Bioreactor™—Part II: Applications for Antibody Production and Cryopreservation," *Biotechnol. Prog.*, 29(3), pp. 768-777, Published online May 21, 2013 (May 21, 2013).

Clincke, M.-F., et al., "Very High Density of CHO Cells in Perfusion by ATF or TFF in WAVE Bioreactor™ Part 1. Effect of the Cell Density on the Process," *Biotechnol Prog.*, 29(3), pp. 754-767, Published online May 21, 2013 (May 21, 2013).

Chen et al., "Temperature Shift as a Process Optimization Step for the Production of Pro-urokinase by a Recombinant Chinese Hamster Ovary Cell Line in High-Density Perfusion Culture", Journal of Bioscience and Bioengineering, 2004, 97(4): 239-243.

* cited by examiner

CELL CULTURE PROCESS BY INTENSIFIED PERFUSION WITH CONTINUOUS HARVEST AND WITHOUT CELL BLEEDING

CROSS-REFERENCE

This application claims priority to International Patent Application No. PCT/CN2018/113776, filed on Nov. 2, 2018, and International Patent Application No. PCT/CN2019/089993, filed on Jun. 4, 2019. The entire contents of both applications are incorporated herein by reference.

FIELD

The present disclosure relates to method and system for culturing cells and harvesting biologics. More particularly, the present disclosure relates to process for cell culture by intensified perfusion with continuous harvest and without bleeding.

BACKGROUND

Since the inception of biopharmaceutical manufacturing in the 1980s, the demand for greater quantities of therapeutic recombinant proteins continues to grow. Developing manufacturing processes for production of recombinant proteins or other biologic products is a complex endeavor where many variables must be balanced.

In a typical perfusion process, cells are cultured over long periods of time by continuously feeding the cells with fresh media and bleeding the cells to maintain a high cell viability. Regular bleeding of cells from the bioreactor in continuous manufacturing is a typically required, which is inefficient because it causes the loss of cells and the biological product of interest.

In typical cell culture processes, a biological product secreted by the cells is either retained or harvested during the cell culture, depending on the retention system used. In certain circumstances, the cells and the biological product remain in the bioreactor during the culture process. For example, U.S. Pat. No. 9,469,865 discloses a perfusion process in which the cell culture comprising the biological substance and cell culture is circulated over a separation system, wherein the biological substance is retained in or fed back into the reactor and the product is harvested when the culture is terminated. Upon harvest, high packed cell volume results in high difficulty in clarification of the mixture of both the cells and the biological product, resulting in a low overall yield. In other certain circumstances, the cells and the biological product are separated in the bioreactor during the culture process.

Improvements to cell culture processes that can lead to greater product yield, improved product quality and reduced cost are still needed. The present disclosure fulfills at least one of these needs by providing methods and systems for cell culture by intensified perfusion with a continuous harvest and without cell bleeding.

SUMMARY

The current disclosure is directed to a process for producing a biological substance by perfusion culturing of a cell culture in a bioreactor, wherein a basal medium and a feed medium are fed to the cell culture at different rates and wherein the cell culture is passed through a separation system to continuously harvest the biological substance. During the culture process, cells are retained in the bioreactor without bleeding. The process of the present disclosure provides a considerable advantage in terms of PVCD (peak viable cell density) and Qp (Cell specific productivity). As a result, the present process can result in an improved productivity of the desired biological substance.

It has been found that by feeding a basal medium and a feed medium to the cell culture at different rates, by shifting the temperature during the culture, and by not bleeding the cell culture, a high amount of biomass at an early stage and a high productivity at a later stage can be achieved. Also, a coordinated separation system which continuously harvests the biological substance helps achieve a high Qp, a better quality of biological substance and/or a high purification yield. The method of the disclosure is referred to as an intensified perfusion culture (IPC) process, wherein a perfusion process is coordinated with a continuous harvest process and wherein the bleeding process is omitted.

Specifically, the present disclosure provides a method for producing a biological substance comprising (a) culturing a cell culture comprising a cell culture medium and cells, (b) perfusing the cell culture in a bioreactor with a basal medium and a feed medium, and (c) harvesting the biological substance, wherein the basal medium and the feed medium are fed to the cell culture at different rates, the cell culture is continuously passed through a separation system, and cells are retained during the entire culture process in the bioreactor without bleeding.

In at least one embodiment, a cell culture is established by inoculating cells expressing a biological substance of interest in a bioreactor. In another embodiment, the cell culture is established by inoculating at least $0.1\times10^6$ viable cells/mL in a bioreactor. In another embodiment, the cell culture is established by inoculating about $0.7$-$0.8\times10^6$ viable cells/mL, about $0.8$-$1.0\times10^6$ viable cells/mL, about $1.0$-$4.0\times10^6$ viable cells/mL. In another embodiment, the cell culture is established by inoculating about $0.1$-$4.0\times10^6$ viable cells/mL, $0.1$-$0.5\times10^6$ viable cells/mL, about $0.5$-$1.0\times10^6$ viable cells/mL, about $1.0$-$1.5\times10^6$ viable cells/mL, about $1.5$-$2.0\times10^6$ viable cells/mL, about $2.0$-$2.5\times10^6$ viable cells/mL, about $2.5$-$3.0\times10^6$ viable cells/mL, about $3.0$-$3.5\times10^6$ viable cells/mL, about $3.5$-$4.0\times10^6$ viable cells/mL, about $0.2$-$0.4\times10^6$ viable cells/mL, about $0.4$-$0.6\times10^6$ viable cells/mL, about $0.6$-$0.8\times10^6$ viable cells/mL, about $0.8$-$1.0\times10^6$ viable cells/mL, about $1.0$-$1.2\times10^6$ viable cells/mL, about $1.2$-$1.4\times10^6$ viable cells/mL, about $1.4$-$1.6\times10^6$ viable cells/mL, about $1.6$-$1.8\times10^6$ viable cells/mL, or about $1.8$-$2.0\times10^6$ viable cells/mL.

The cell culture is maintained by perfusing a basal medium and a feed medium at different rates. In at least one embodiment of the disclosure, the perfusion of the feed medium is at a rate of about 0.1-20% of the perfusion rate of the basal medium, such as about 1%, about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, or about 20% of the perfusion rate of the basal medium. The perfusion rate of the feed medium is adjusted according to cell density, viability and osmolality. In some embodiments, the basal medium is fed at a perfusion rate not higher than 2.0 VVD, such as about 0.1 to not higher than 2.0 VVD, about 0.1 to 1.5 VVD, about 0.3 to 1.2 VVD, or about 0.5 to 1.0 VVD. In some embodiments, the basal medium is fed at a perfusion rate not higher than 2.0 VVD, such as about 0.1 to 2.0 VVD, about 0.1 to 0.3 VVD, about 0.3 to 0.6 VVD, about 0.6 to 0.9 VVD, about 0.9 to 1.2 VVD, about 1.2 to 1.5 VVD, about 1.5 to 1.8 VVD, about 1.8 to 2.0 VVD, about 0.5 to 1.0 VVD, about 0.7 to 1.2

VVD, or about 1.0 to 1.5 VVD. In some embodiments, the perfusion of the feed medium is at a rate of about 1-15%, preferably about 1-10%, more preferably about 1-9% of the perfusion rate of the basal medium. In some embodiments, the perfusion of the feed medium is at a rate of about 1-15%, about 1-14%, about 1-13%, about 1-12%, about 1-11%, about 1-10%, about 1-9%, about 1-8%, about 1-7%, about 1-6%, about 1-5%, about 1-4%, about 1-3%, about 1-2%, about 2-9%, about 3-9%, about 4-9%, about 5-9%, about 6-9%, or about 7-9% of the perfusion rate of the basal medium. The feeding rate of the basal medium may be increased as cell density increases and may reach the target feeding rate (e.g., on Day 3 to Day 6) before the cell density reaches the peak, then the target feeding rate may be fixed until culture termination. In at least one embodiment of the present disclosure, the feeding rate of basal medium is increased on Day 1, Day 2, Day 3, Day 4, Day 5, Day 6, Day 7, or Day 8 of the culture process. The feeding rate of the feed medium may be increased as cell density increases to supply sufficient nutrition, normally start from Day 2 to Day 4, and may reach the peak on Day 6 to Day10, and sometimes may be decreased during cell culture as cell density or viability decreases. In at least one embodiment of the present disclosure, the feeding rate of the feed medium is increased on Day 1, Day 2, Day 3, Day 4, Day 5, Day 6, Day 7, or Day 8 of the culture process. In another embodiment, the feeding rate of the feed medium reaches the peak on Day 3, Day 4, Day 5, Day 6, Day 7, Day 8, Day 9, Day 10, Day 11, Day 12, Day 13, or Day 14.

In at least one embodiment the method as disclosed herein further comprises subjecting the cell culture to a temperature shift. The purpose of temperature shift is to repress over-growth of cells before the VCD reaches the peak. In at least one embodiment of the present disclosure, the temperature shift is in response to a predetermined parameter such as peak VCD. In another embodiment, the temperature shift occurs on Day 3, Day 4, Day 5, Day 6, Day 7, Day 8, Day 9, Day 10, Day 11, Day 12, Day 13, or Day 14. In at least one embodiment, the temperature shift may be for instance a temperature shift from around 35-37° C. to around 28-33° C., or from around 34-36° C. to around 27-34° C., or from around 36-38° C. to around 29-34° C., or from around 36-39° C. to around 30-35° C., or from around 33-35° C. to around 26-31° C.

In at least one embodiment, the biological substance produced is continuously harvested by the separation system with a hollow fiber filter. In at least one embodiment, the pore size or molecular weight cut-off of the hollow fiber filter is chosen such that the hollow fiber filter does not retain the biological substance of interest but retains the cells. Therefore, the biological substance produced by the cells are harvested and the cells are retained in the culture. In some embodiments, the pore size of the hollow fiber filter is about 0.08 μm to about 0.5 μm, preferably about 0.1 μm to about 0.5 μm, more preferably about 0.2 μm or about 0.45 μm. In at least one embodiment, the pore size of the hollow fiber filter is about 0.08 μm to about 1.0 μm, such as about 0.1 μm to about 0.8 μm, about 0.1 μm to about 0.6 μm, about 0.1 μm to about 0.5 μm, about 0.1 μm to about 0.4 μm, about 0.1 μm to about 0.3 μm, about 0.2 μm to about 0.8 μm, about 0.2 μm to about 0.8 μm, about 0.3 μm to about 0.8 μm, about 0.4 μm to about 0.8 μm, about 0.2 μm to about 0.6 μm, about 0.2 μm to about 0.5 μm. In at least one embodiment, the hollow fiber filter is about 0.2 μm or about 0.45 μm.

In at least one embodiment, the separation system with a hollow fiber filter is an Alternating tangential flow (ATF) or Tangential flow filtration (TFF) device.

In at least one embodiment, cells are retained in the bioreactor during the whole culture process without bleeding. It was found that it was possible to obtain a high level of cell density by omitting the bleeding system.

In at least one embodiment, the harvested materials were subjected to a continuous product capture by chromatography steps. It has surprisingly been found that by adopting the continuous product capture process, a highly productive (e.g., ultra-highly productive) cell culture can be achieved.

Also provided herein is a system for producing a biological substance, which system comprises: a) a module for perfusing a cell culture in a bioreactor with a basal medium and a feed medium at different rates; and b) a module for continuously harvesting the biological substance, comprising a hollow fiber filter having a pore size or a molecular weight cut-off (MWCO) larger than the molecular weight of the biological substance, such that it does not retain the biological substance of interest but retains the cells, preferably, the module for continuously harvesting the biological substance is an Alternating tangential flow (ATF) device; and c) optionally, a module for continuous capture of the biological substance from the harvested materials. In some embodiments, the system further comprises a bioreactor for cell culture and/or a microsparger.

DETAILED DESCRIPTION

I. Definitions

Figure 1A:
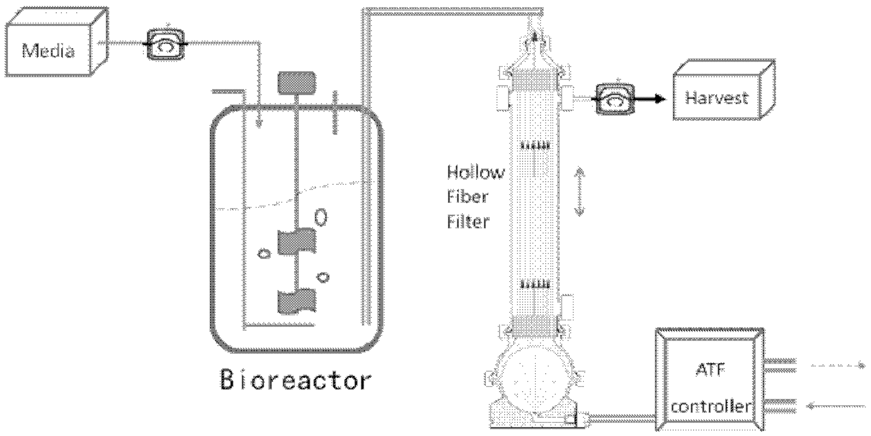
FIG. 1*a* is a schematic diagram of a culture system according to at least one embodiment of the present disclosure.
Figure 1B:
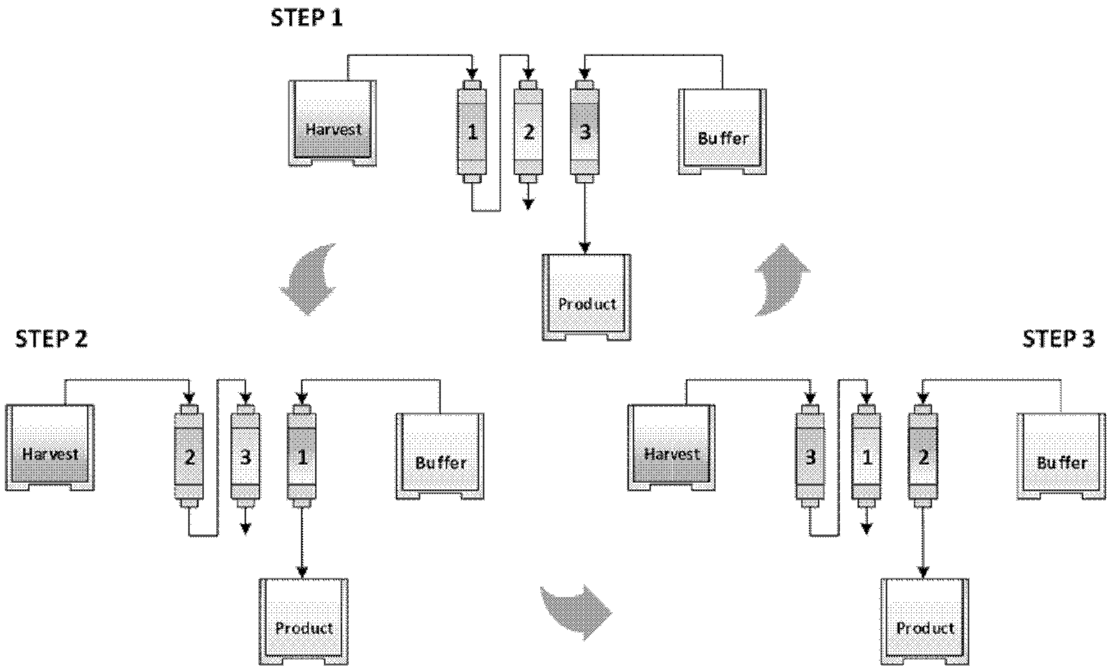
FIG. 1*b* is a schematic diagram of a continuous product capture system according to at least one embodiment of the present disclosure.

Unless defined otherwise, all technical and scientific terms used herein have the same meaning as is commonly understood by one of ordinary skill in the art to which this disclosure belongs. All patents, applications, published applications and other publications referred to herein are incorporated by reference in their entirety. If a definition set forth in this section is contrary to or otherwise inconsistent with a definition set forth in the patents, applications, published applications and other publications that are herein incorporated by reference, the definition set forth in this section prevails over the definition that is incorporated herein by reference.

As used herein, the singular forms "a", "an", and "the" include plural references unless indicated otherwise. For example, "a" biological substance includes one or more biological substances.

A "bioreactor" as used herein is a system that can comprise a cell culture which cell culture on its turn comprises cells and a cell culture medium. In some embodiments, it provides sterile barriers, such as air filters, to prevent other cells from contaminating the desired cells. In some embodiments, it maintains a favorable environment for the cells by providing the suitable culture conditions such as mixing, temperature, pH, oxygen concentration etc.

By "cell culture" or "culture" is meant the growth and propagation of cells outside of a multicellular organism or tissue. "Cell culture" includes the liquid comprising a cell culture medium, cells and a biological substance, which liquid is the result of a process for the culturing of cells in a reactor in a cell culture medium, wherein the cells produce the biological substance. Suitable culture conditions for mammalian cells are known in the art. See e.g. Animal cell culture: A Practical Approach, D. Rickwood, ed., Oxford University Press, New York (1992). Mammalian cells may be cultured in suspension or while attached to a solid substrate.

By "cells" is meant cells that produce a biological substance of interest, for instance cells capable of expressing a gene encoding the product. Cells capable of expressing a gene encoding the product may for example be prepared by transfection of the cells with a plasmid containing the gene encoding the cell product and gene encoding a suitable selection marker. Cells which can be used to produce the product are in principle all cells known to the person skilled in the art, which have the ability to produce a biological product. The cells may be animal cells, in particular mammalian cells. Examples of mammalian cells include CHO (Chinese Hamster Ovary) cells, hybridomas, BHK (Baby Hamster Kidney) cells, myeloma cells, human cells, for example HEK-293 cells, human lymphoblastoid cells, E1 immortalized HER cells, mouse cells, for example NS0 cells.

As used herein, the term "cell culturing medium" (also called "culture medium" "cell culture media") refers to any nutrient solution used for growing cells, e.g., animal or mammalian cells, and which generally provides at least one or more components from the following: an energy source (usually in the form of a carbohydrate such as glucose); one or more of all essential amino acids, and generally the twenty basic amino acids, plus cysteine; vitamins and/or other organic compounds typically required at low concentrations; lipids or free fatty acids; and trace elements, e.g., inorganic compounds or naturally occurring elements that are typically required at very low concentrations, usually in the micromolar range.

A "basal cell culture medium" refers to a cell culture medium that is typically used to initiate a cell culture and is sufficiently complete to support the cell culture. Commercially available basal medium can be utilized and include, but is not limited to media specialized for CHO cell culture such as CD OPTICHO™ AGT™ (Invitrogen), CD CHO AGT™ (Invitrogen), DYNAMIS™ AGT™ Medium (Invitrogen), SFM4CHO ADCF (Hyclone Laboratories Inc.), HyCell CHO Medium (Hyclone Laboratories Inc.), CDM4MAB (Hyclone Laboratories Inc.), DPM HYCLONE™ ACTIPRO™ (Hyclone Laboratories Inc.), and Advanced CHO Fed-batch Medium (Sigma).

A "feed" cell culture medium or feed medium refers to a cell culture medium that is typically used in cell cultures during a period of exponential growth, a "growth phase", and is sufficiently complete to support the cell culture during this phase. A growth cell culture medium may also contain one or more selection agents that confer resistance or survival to selectable markers incorporated into the host cell line. Such selection agents include, but are not limited to, geneticin (G4118), neomycin, hygromycin B, puromycin, zeocin, methionine sulfoximine, methotrexate, glutamine-free cell culture medium, cell culture medium lacking glycine, hypoxanthine and thymidine, or thymidine alone. Commercially available feed medium can be utilized and include, but is not limited to CHO CD EFFICIENTFEED™ A (Invitrogen), CHO CD EFFICIENTFEED™ B (Invitrogen), CHO CD EFFICIENTFEED™ C (Invitrogen), Sheff-CHO PLUS PF ACF (FM012) (Kerry), CHO CD EFFICIENTFEED™ A+ (Invitrogen), CHO CD EFFICIENTFEED™ B+ (Invitrogen), CHO CD EFFICIENTFEED™ C+ (Invitrogen), DPM-CELL BOOST™ 7a (Hyclone Laboratories Inc.), DPM-CELL BOOST™ 7b (Hyclone Laboratories Inc.), or FAA01A (Hyclone Laboratories Inc.).

Cell culture medium, in certain embodiments, is serum-free and/or free of products or ingredients of animal origin. Cell culture medium, in certain embodiments, is chemically defined, where all of the chemical components are known. Commercially available media can be utilized and supplementary components or ingredients, including optional components, in appropriate concentrations or amounts, as necessary or desired, can be added, as would be known and practiced by those having in the art using routine skill.

In the context of the present disclosure, the terms "product," "biologic" and "biological substance" are interchangeable. Products, which may be produced by the cells, for example by expressing a (recombinant) gene coding therefore are for example (recombinant) proteins, in particular receptors, enzymes, fusion proteins, blood proteins such as proteins from the blood coagulation cascade, multifunctional proteins such as for instance erythropoietin, virus or bacterial proteins for instance for use in vaccines; immunoglobulins such as antibodies, for example IgG or IgM, multi-specific antibodies such as bi-specific antibodies and the like. Preferably a protein, more preferably an antibody is produced by the cells.

The term "antibody" includes reference to both glycosylated and non-glycosylated immunoglobulins of any isotype or subclass or to an antigen-binding region thereof that competes with the intact antibody for specific binding, unless otherwise specified, including human, humanized, chimeric, multi-specific, monoclonal, polyclonal, and oligomers or antigen binding fragments thereof. Also included are proteins having an antigen binding fragment or region such as Fab, Fab', F(ab')2, Fv, diabodies, Fd, dAb, maxibodies, single chain antibody molecules, complementarity determining region (CDR) fragments, scFv, diabodies, triabodies, tetrabodies and polypeptides that contain at least a portion of an immunoglobulin that is sufficient to confer specific antigen binding to a target polypeptide. The term "antibody" is inclusive of, but not limited to, those that are prepared, expressed, created or isolated by recombinant means, such as antibodies isolated from a host cell transfected to express the antibody.

Examples of antibodies include, but are not limited to, those that recognize any one or a combination of proteins including, but not limited to, the above-mentioned proteins and/or the following antigens: CD2, CD3, CD4, CD8, CD11a, CD14, CD18, CD20, CD22, CD23, CD25, CD33, CD40, CD44, CD52, CD80 (B7.1), CD86 (B7.2), CD147, IL-1α, IL-1β, IL-2, IL-3, IL-7, IL-4, IL-5, IL-8, IL-10, IL-2 receptor, IL-4 receptor, IL-6 receptor, IL-13 receptor, IL-18 receptor subunits, FGL2, PDGF-β and analogs thereof (see U.S. Pat. Nos. 5,272,064 and 5,149,792), VEGF, TGF, TGF-β2, TGF-β1, EGF receptor (see U.S. Pat. No. 6,235,883), VEGF receptor, hepatocyte growth factor, osteoprotegerin ligand, interferon gamma, B lymphocyte stimulator (BlyS, also known as BAFF, THANK, TALL-1, and zTNF4; see Do and Chen-Kiang (2002), Cytokine Growth Factor Rev. 13(1): 19-25), C5 complement, IgE, tumor antigen CA125, tumor antigen MUC1, PEM antigen, LCG (which is a gene product that is expressed in association with lung cancer), HER-2, HER-3, a tumor-associated glycoprotein TAG-72, the SK-1 antigen, tumor-associated epitopes that are present in elevated levels in the sera of patients with colon and/or pancreatic cancer, cancer-associated epitopes or proteins expressed on breast, colon, squamous cell, prostate, pancreatic, lung, and/or kidney cancer cells and/or on melanoma, glioma, or neuroblastoma cells, the necrotic core of a tumor, integrin alpha 4 beta 7, the integrin VLA-4, B2 integrins, TRAIL receptors 1, 2, 3, and 4, RANK, RANK ligand, TNF-α, the adhesion molecule VAP-1, epithelial cell adhesion molecule (EpCAM), intercellular adhesion molecule-3 (ICAM-3), leukointegrin adhesin, the platelet glycoprotein gp IIb/IIIa, cardiac myosin heavy chain, parathyroid hormone, rNAPc2 (which is an inhibitor of factor VIIa-tissue factor), MHC I, carcinoembryonic antigen (CEA), alpha-fetoprotein (AFP), tumor necrosis factor (TNF), CTLA-4 (which is a cytotoxic T lymphocyte-associated antigen), Fc-γ-1 receptor, HLA-DR 10 beta, HLA-DR antigen, sclerostin, L-selectin, Respiratory Syncitial Virus, human immunodeficiency virus (HIV), hepatitis B virus (HBV), *Streptococcus mutans*, and *Staphlycoccus aureus*. Specific examples of known antibodies which can be produced using the methods of the disclosure include but are not limited to adalimumab, bevacizumab, infliximab, abciximab, alemtuzumab, bapineuzumab, basiliximab, belimumab, briakinumab, canakinumab, certolizumab pegol, cetuximab, conatumumab, denosumab, eculizumab, gemtuzumab ozogamicin, golimumab, ibritumomab tiuxetan, labetuzumab, mapatumumab, matuzumab, mepolizumab, motavizumab, muromonab-CD3, natalizumab, nimotuzumab, ofatumumab, omalizumab, oregovomab, palivizumab, panitumumab, pemtumomab, pertuzumab, ranibizumab, rituximab, rovelizumab, tocilizumab, tositumomab, trastuzumab, ustekinumab, vedolizomab, zalutumumab, and zanolimumab.

In some embodiments, the products such as proteins or vaccines produced by the cells can be used as an active ingredient in a pharmaceutical preparation. Non-limiting examples of products includes: anti-hTNFα (Adalimumab (Humira™)), a fusion protein targeting VEGF (Aflibercept (EYLEA™)), erythropoietin alpha (Epogen®), lymphoblastoid Interferon α-n1 (Wellferon™), (recombinant) Coagulation factor (NovoSeven™), Etanercept (Enbrel™), Trastuzumab (Herceptin™), Infliximab (Remicade™), Basiliximab (Simulect™), Daclizumab (Zenapaz™), (recombinant) Coagulation factor IX (Benefix™), Glucocerebrosidase (Cerezyme™), Interferon beta 1b (Betaseron®), G-CSF (Neupogen® Filgrastim), Interferon alpha-2b (Infergen®), recombinant insulin (Humulin®), Interferon beta 1 a (Avonex®), Factor VIII (KoGENate®), Tenecteplase (TNKase™), (recombinant) antihemophilic factor (ReFacto™), TNF alpha receptor (Enbrel®), Follicle stimulating hormone (Gonal-F®), Mab abciximab (Synagis®, ReoPro®), Mab ritiximab (Rituxan®), tissue plasminogen activator (Activase®, Actilyase®), human growth hormone (Protropin®, Norditropin®, GenoTropin™). Furthermore, the definition of the term "antibody construct" includes monovalent, bivalent and polyvalent/multivalent constructs and, thus, bispecific constructs, specifically binding to only two antigenic structure, as well as polyspecific/multispecific constructs, which specifically bind more than two antigenic structures, e.g. three, four or more, through distinct binding domains. Moreover, the definition of the term "antibody construct" includes molecules consisting of only one polypeptide chain as well as molecules consisting of more than one polypeptide chain, which chains can be either identical (homodimers, homotrimers or homo oligomers) or different (heterodimer, heterotrimer or heterooligomer). Examples for the above identified antibodies and variants or derivatives thereof are described inter alia in Harlow and Lane, Antibodies a laboratory manual, CSHL Press (1988) and Using Antibodies: a laboratory manual, CSHL Press (1999), Kontermann and Dubel, Antibody Engineering, Springer, 2nd ed. 2010 and Little, Recombinant Antibodies for Immunotherapy, Cambridge University Press 2009.

As used herein, the term "polypeptide" refers to a molecule composed of monomers (amino acids) linearly linked by amide bonds (also known as peptide bonds). The term "polypeptide" refers to any chain of two or more amino acids, and does not refer to a specific length of the product. Thus, peptides, dipeptides, tripeptides, oligopeptides, "protein," "amino acid chain," or any other term used to refer to a chain of two or more amino acids, are included within the definition of "polypeptide," and the term "polypeptide" may be used instead of, or interchangeably with any of these terms. The term "polypeptide" is also intended to refer to the products of post-expression modifications of the polypeptide, including without limitation glycosylation, acetylation, phosphorylation, amidation, derivatization by known protecting/blocking groups, proteolytic cleavage, or modification by non-naturally occurring amino acids. A polypeptide may be derived from a natural biological source or produced by recombinant technology, but is not necessarily translated from a designated nucleic acid sequence. It may be generated in any manner, including by chemical synthesis. A polypeptide of the disclosure may be of a size of about 3 or more, 5 or more, 10 or more, 20 or more, 25 or more, 50 or more, 75 or more, 100 or more, 200 or more, 500 or more, 1,000 or more, or 2,000 or more amino acids. Polypeptides may have a defined three-dimensional structure, although they do not necessarily have such structure. Polypeptides with a defined three-dimensional structure are referred to as folded, and polypeptides which do not possess a defined three-dimensional structure, but rather can adopt a large number of different conformations, and are referred to as unfolded.

The term "aggregation" generally refers to the direct mutual attraction between molecules, e.g., via van der Waals forces or chemical bonding. In particular, aggregation is understood as proteins accumulating and clumping together, i.e., "aggregates" and "fragments." Aggregates may include amorphous aggregates, oligomers, and amyloid fibrils and are typically referred to as high molecular weight (HMW) species, i.e., molecules having a higher molecular weight than pure product molecules which are non-aggregated molecules, typically referred to herein also as low molecular weight (LMW) species or monomer.

The term "microsparger" generally refers to a sparger configured to provide oxygen and/or other gases to a cell culture within a bioreactor tank. An aerator or microsparger may be coupled to a source of oxygen or other gas, and may direct the gas to the cell culture so that the gas bubbles in the cell culture, thereby aerating the cell culture. In some examples, a microsparger may be used in combination with a drilled tube sparger.

Biologics prepared as described herein may be purified by art-known techniques such as high performance liquid chromatography, ion exchange chromatography, gel electrophoresis, affinity chromatography, size exclusion chromatography (SEC), and the like. The actual conditions used to purify a particular protein will depend, in part, on factors such as net charge, hydrophobicity, hydrophilicity etc., and will be apparent to those having skill in the art. For affinity chromatography purification an antibody, ligand, receptor or antigen can be used to which the biologic binds. For example, for affinity chromatography purification of a biologic (e.g., immunoconjugates) of the disclosure, a matrix with protein A or protein G may be used. Sequential Protein A or G affinity chromatography and size exclusion chromatography can be used to isolate a biologic, e.g., an immunoconjugate, e.g., as described in the Examples. The purity of the biologic (e.g., immuno-conjugate) can be determined by any of a variety of well-known analytical methods including gel electrophoresis, high pressure liquid chromatography, and similar methods.

II. Perfusion Culture Process

A "perfusion" culturing process is one in which the cell culture receives the addition of fresh medium and spent medium is removed from the bioreactor. Perfusions can be continuous, stepwise, intermittent, or a combination of any or all of any of these.

In various embodiments, a cell culture is established by inoculating cells expressing a biological substance of interest in a bioreactor, for example, with at least $0.1\times10^6$ viable cells/mL, for example about $0.7\text{-}0.8\times10^6$ viable cells/mL, about $0.8\text{-}1.0\times10^6$ viable cells/mL, about $1.0\text{-}4.0\times10^6$ viable cells/mL. In at least one embodiment, a cell culture is established by inoculating cells expressing a biological substance of interest in a bioreactor, for example, with at least $0.1\times10^6$ viable cells/mL, for example about $0.1$-$4.0\times10^6$ viable cells/mL, $0.1$-$0.5\times10^6$ viable cells/mL, about $0.5$-$1.0\times10^6$ viable cells/mL, about $1.0$-$1.5\times10^6$ viable cells/mL, about $1.5$-$2.0\times10^6$ viable cells/mL, about $2.0$-$2.5\times10^6$ viable cells/mL, about $2.5$-$3.0\times10^6$ viable cells/mL, about $3.0$-$3.5\times10^6$ viable cells/mL, about $3.5$-$4.0\times10^6$ viable cells/mL, about $0.2$-$0.4\times10^6$ viable cells/mL, about $0.4$-$0.6\times10^6$ viable cells/mL, about $0.6$-$0.8\times10^6$ viable cells/mL, about $0.8$-$1.0\times10^6$ viable cells/mL, about $1.0$-$1.2\times10^6$ viable cells/mL, about $1.2$-$1.4\times10^6$ viable cells/mL, about $1.4$-$1.6\times10^6$ viable cells/mL, about $1.6$-$1.8\times10^6$ viable cells/mL, or about $1.8$-$2.0\times10^6$ viable cells/mL.

The cell culture is maintained by feeding the basal medium and a feed medium. The cells may be cultured in the basal medium for one day before feeding the medium. For example, perfusion of basal medium may be started from Day 2, with perfusion of feed medium stated from Day 3. Alternatively, perfusion of basal medium may be started from Day 1. As another example, perfusion of basal medium may be started from Day 1, Day 2, Day 3, Day 4, Day 5, Day 6, or Day 7, with perfusion of feed medium started from Day 2, Day 3, Day 4, Day 5, Day 6, or Day 7.

The term "perfusion rate" is the amount of media that is passed through (added and removed) from a bioreactor, typically expressed as some portion of or a multiple of the working volume, in a given time. "Working volume" refers to the amount of bioreactor volume used for cell culture. In at least one embodiment, the perfusion rate of the basal medium could be not higher than 2.0 working volume per day (VVD), for example about 0.1 to 1.5 VVD, about 0.3 to 1.2 VVD, or about 0.5 to 1.0 VVD.

The rate of addition of cell culture medium to the culture may influence the viability and the density of the cells. It has been surprisingly found that by adjusting the feeding rate of the basal medium and the feed medium and feeding them at different stages, a high viable cell density (VCD) and viability can be achieved. The term "viable cell density" refers to the number of live cells in a given volume of culture medium, as determined by standard viability assays (such as trypan blue dye exclusion method).

In various embodiments, the basal medium and the feed medium are fed to the cell culture at different perfusion rates, with the provision that the perfusion of the feed medium is at a rate of about 0-20% of the perfusion rate of the basal medium, for example, the perfusion of the feed medium is at a rate of about 0.1-20% of the perfusion rate of the basal medium, such as about 1%, about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, or about 20% of the perfusion rate of the basal medium. In at least one embodiment of the present disclosure, the perfusion rate of the basal medium is not higher than about 2.0 VVD, such as about 0.1 to 1.5 VVD, about 0.3 to 1.2 VVD, or about 0.5 to 1.0 VVD. For example, perfusion of the basal medium may be started from Day 1 with a rate of about 0.4 VVD and the rate may be increased to about 1.5 VVD on Day 3 and kept at about 1.5 VVD until end of culture. The perfusion of the feed medium may be started from Day 4 at a rate of about 2.0% of basal medium and be increased to about 4.0% of basal medium on Day 7 and be decreased gradually from Day 8 to about 1% on Day 17. In another embodiment, perfusion of the basal medium may be started from Day 1 with a rate of about 0.4 VVD and the rate may be increased to about 1.5 VVD on Day 4 and kept at about 1.5 VVD until end of culture. The perfusion of the feed medium may be started from Day 5 at a rate of about 2.0% of basal medium and be increased to about 9% of basal medium on Day 12 and be decreased to about 7% on Day 18 and maintained at about 6% from Day 19 until termination. In another embodiment, perfusion of the basal medium may be started from Day 2 with a rate of about 0.6 VVD and the rate may be increased to about 0.88 VVD on Day 6 and kept at about 0.88 VVD until end of culture. The perfusion of the feed medium may be started from Day 2 at a rate of about 6.7% of basal medium and be increased to about 16% of basal medium on Day 12 and be kept at about 16% until termination.

III. Cell Culture Controls

Cell culture conditions suitable for the methods of the present disclosure are those that are typically employed and known for perfusion culturing of cells or any combination of those methods, with attention paid to pH, dissolved oxygen ($O_2$), and carbon dioxide ($CO_2$), agitation and aeration, and temperature.

During recombinant protein or biologic production, it may be desirable to have a controlled system where cells are grown for a desired time or to a desired density and then the physiological state of the cells is switched to a growth-limited or arrested, high productivity state where the cells use energy and substrates to produce the recombinant protein in favor of increasing cell density. For commercial scale cell culture and the manufacture of biological therapeutics, the ability to limit or arrest cell growth and being able to maintain the cells in a growth-limited or arrested state during the production phase is very desirable. Such methods include, for example, temperature shifts.

One such mechanism for limiting or arresting growth is to shift the temperature during the cell culture. For example, a growth phase may occur at a higher temperature, shifting to a lower temperature may initiate and/or maintain a production phase. For example, a growth phase may occur at a first temperature set-point from about 35° C. to about 37° C., and a production phase may occur at a second temperature set-point from about 28° C. to about 33° C. In a related embodiment, the temperature shift is in response to a predetermined parameter such as peak VCD. In at least one embodiment, the temperature shift may be for instance a temperature shift from around 35-37° C. to around 28-33° C. In at least one embodiment, a growth phase may occur at a first temperature set-point from about 30° C. to about 38° C., such as from about 31° C. to about 37° C., from about 32° C. to about 36° C., from about 33° C. to about 35° C., from about 33° C. to about 34° C., from about 32° C. to about 35° C., or from about 31° C. to about 34° C. In at least one embodiment, a production phase may occur at a second temperature set-point from about 25° C. to about 35° C., such as 25° C. to about 30° C., 30° C. to about 35° C., 26° C. to about 31° C., 27° C. to about 32° C., 28° C. to about 33° C., or 29° C. to about 34° C. In another embodiment, the temperature shift is in response to a predetermined parameter such as peak VCD. In at least one embodiment, the temperature shift may be for instance a temperature shift from around 35-37° C. to around 28-33° C., such as from around 34-36° C. to around 27-34° C., from around 36-38° C. to around 29-34° C., from around 36-39° C. to around 30-35° C., or from around 33-35° C. to around 26-31° C.

Switching the temperature set-point can be done manually or can be done automatically by making use of bioreactor control systems. The temperature set-point may be switched at a predetermined time or in response to one or more cell culture parameters, such as cell density, titer, or concentration of one or more media components.

One advantage of the process of the present disclosure is that a bleeding step is not required. It has been surprisingly found that by feeding a basal medium and a feed medium to the cell culture at different rates and adopting a temperature shift strategy and by omitting bleeding of the cells, a high amount of biomass at early stage and a high productivity at a later stage can be achieved. By omitting a bleeding step, cells are kept at a non-steady state and the cell density is pushed to a very high level. To maintain a high VCD and viability, the process of the present disclosure utilizes temperature shifting and different feeding rates of the basal and feed media.

In at least one embodiment of the present disclosure, an antifoam is added to the bioreactor before inoculation of cells. In at least one embodiment of the present disclosure, about 5 to 20 ppm, about 8 to 15 ppm, about 9 to 12 ppm, or about 10 ppm of antifoam is added to the bioreactor before inoculation of cells. In at least one embodiment of the present disclosure, about 5 to 200 ppm, about 8 to 150 ppm, about 9 to 120 ppm, about 10 to 100 ppm of antifoam is added to the culture medium during culture. The antifoam can be added every day, every 2 days, every 3 days, every four days, or once.

The terms "anti-foaming agent" and "defoamer" are used interchangeably in the context of the present disclosure. In at least one embodiment of the present disclosure, the antifoam can be any agent which reduces and hinders the formation of foam in cultures. In the present disclosure, addition of antifoam before inoculation alleviates cell damage caused by bubbles burst during culture. In at least one embodiment of the present disclosure, any antifoam which can attain the technical effect of the present application can be used. In at least one embodiment of the present disclosure, the antifoam includes, but not limited to, oil-based defoamers, powder defoamers, water-based defoamers, silicone-based defoamers, EO/PO based defoamers, or Alkyl polyacrylates. In a further embodiment of the present disclosure, the oil in the oil-based defoamer might be mineral oil, vegetable oil, white oil or any other oil that is insoluble in the foaming medium, except silicone oil. In a further embodiment of the present disclosure, the oil-based defoamer also contains a wax and/or hydrophobic silica to boost the performance. Typical waxes are ethylene bis stearamide (EBS), paraffin waxes, ester waxes and fatty alcohol waxes. In at least one embodiment of the present disclosure, the powder defoamers are in principle oil based defoamers on a particulate carrier like silica. These are added to powdered products like cement, plaster and detergents. In at least one embodiment of the present disclosure, the water based defoamers are different types of oils and waxes dispersed in a water base in which the oils are often mineral oil or vegetable oils and the waxes are long chain fatty alcohol, fatty acid soaps or esters. In at least one embodiment of the present disclosure, the silicone-based defoamers are polymers with silicon backbones in which the silicone compound consists of a hydrophobic silica dispersed in a silicone oil, and might also contain silicone glycols and other modified silicone fluids. In at least one embodiment of the present disclosure, the EO/PO based defoamers contain polyethylene glycol and polypropylene glycol copolymers which have good dispersing properties and are often well suited when deposit problems are an issue. In at least one embodiment of the present disclosure, the alkyl polyacrylates are suitable for use as defoamers in non-aqueous systems where air release is more important than the breakdown of surface foam.

In at least one embodiment of the present disclosure, a microsparger is used in the method of the present disclosure. In further embodiment of the present disclosure, the microsparger is used when demanded oxygen flow rate reaches about 0.2 VVM. In the present disclosure, the implement of microsparger alleviates cell damage caused by bubbles burst during culture.

IV. Continuous Harvest

In various embodiments, the cells are retained in the culture while the biological substance of interest produced by the cells are continuously harvested from the cell culture. In this regard, a separation system with a hollow fiber filter is connected to the perfusion system. The pore size or molecular weight cut-off of the hollow fiber filter is chosen such that the hollow fiber filter does not retain the biological substance of interest but retains the cells. When the cell culture, including cell culture media, cells (e.g., whole and lysed), soluble expressed recombinant proteins, host cell proteins, waste products and the like, are introduced to the filter, the hollow fiber material may retain certain cell culture components on the lumen side and allow the biological substance of interest to pass through the filter. The cells that are retained are returned to the bioreactor. The cell culture may be drawn out of the bioreactor and into the filter by a pumping system, which passes the cell culture through the lumen side of the hollow fiber.

In various embodiments, any filter may be used as the separation system, as long as the pore size or molecular weight cut-off (MWCO) is chosen such that the cells but not the biological substance of interest is retained. Non-limiting examples of filters suitable for use in the present disclosure include membrane filters, ceramic filters and metal filters. The filter may be used in any shape; the filer may for example be spiral wound or tubular or may be used in the form of a sheet. In various embodiments, the filter used is a membrane filter. In at least one embodiment, the filter is a hollow fiber filter. In at least one embodiment, the pore size of the hollow fiber filter is about 0.08 μm to 0.5 μm, about 0.1 μm to 0.5 μm, about 0.2 μm or about 0.45 μm. In at least one embodiment, the pore size of the hollow fiber filter is about 0.08 μm to about 1.0 μm, such as about 0.1 μm to about 0.8 μm, about 0.1 μm to about 0.6 μm, about 0.1 μm to about 0.5 μm, about 0.1 μm to about 0.4 μm, about 0.1 μm to about 0.3 μm, about 0.2 μm to about 0.8 μm, about 0.2 μm to about 0.8 μm, about 0.3 μm to about 0.8 μm, about 0.4 μm to about 0.8 μm, about 0.2 μm to about 0.6 μm, or about 0.2 μm to about 0.5 μm. In at least one embodiment, the hollow fiber filter is about 0.2 μm or about 0.45 μm. Filter modules comprising hollow fibers are commercially available from, for example, Refine Technology.

By circulating the cell culture comprising the biological substance, cells and the cell culture medium over a separation system, the cells are retained in the reactor and the biological substance of interest are harvested. The circulation of the cell culture may start when the perfusion process started, for example, on Day 2 or Day 3.

The circulation of the cell culture over a filter may be a flow substantially perpendicular with respect to the filter surface, also known as dead-end flow or a flow substantially parallel to the filter surface, also known as tangential flow, for example unidirectional tangential flow (TFF) or cross-flow. A preferred example of cross-flow is alternating tangential flow (ATF) as with ATF it was found that filter clogging does not occur (quickly) even at very high cell densities.

With "alternating tangential flow" is meant that there is one flow in the same direction as (i.e. tangential to) the filter surface(s), which flow is going back and forth, and that there is another flow in a direction substantially perpendicular to said filter surface. Alternating tangential flow can be achieved according to methods known to a person skilled in the art (for example as described to U.S. Pat. No. 6,544,424 which is incorporated herein by reference in its entirety).

In at least one embodiment, the biological substance produced by the cells is continuously harvested by a separation system with a hollow fiber filter having a pore size of about 0.08 μm to 0.5 μm, about 0.1 μm to 0.5 μm, about 0.2 μm or about 0.45 μm. In at least one embodiment, the biological substance produced by the cells is continuously harvested by a separation system with a hollow fiber filter having a pore size of about 0.08 μm to about 1.0 μm, such as about 0.1 μm to about 0.8 μm, about 0.1 μm to about 0.6 μm, about 0.1 μm to about 0.5 μm, about 0.1 μm to about 0.4 μm, about 0.1 μm to about 0.3 μm, about 0.2 μm to about 0.8 μm, about 0.2 μm to about 0.8 μm, about 0.3 μm to about 0.8 μm, about 0.4 μm to about 0.8 μm, about 0.2 μm to about 0.6 μm, or about 0.2 μm to about 0.5 μm. In at least one embodiment, the hollow fiber filter is about 0.2 μm or about 0.45 μm.

V. Downstream Purification

The biological substances produced in the process of the present disclosure can be further captured from the harvest material in a so-called downstream processing. Downstream processing usually includes several purification steps in varying combinations and order. Non-limiting examples of purification steps in the downstream processing are separation steps (e.g., by affinity chromatography and/or ion exchange chromatography and/or extraction by aqueous two-phase systems and/or precipitation by for example ammonium sulphate), steps for the concentration of the biological substance (e.g., by ultrafiltration or diafiltration), steps to exchange buffers and/or steps to remove or inactivate viruses (e.g., by virus filtration, pH shift or solvent detergent treatment).

In at least one embodiment of the present disclosure, the harvested materials from the ATF device are subjected to a continuous product capture by chromatography steps. For example, multiple column chromatography systems such as simulated moving beds (SMB), periodic counter current chromatography (PCC) and two column chromatography (TCC) may be used for continuous product capture. In some embodiments of the present disclosure, the harvested materials from the ATF device are subjected to a continuous product capture by chromatography steps, using for example 2-16 columns preferably 3-8 columns, more preferably 3 columns, packed with appropriate resin (with different functional ligand such as Protein A, IEX, HIC, mixed-mode, IMAC, etc.) depending on the nature of the product to be captured. In the load phase and post-load wash phase, two or more (2-15) columns are connected in tandem, while in other phases, the rest column(s) are processed with different buffer at different phases. Particularly, for a 2-column process, one column is used to collect the harvest at the beginning, while the second column is used for the non-loading phase. When the non-loading phases are done, the second column is connected to the outlet of the first column to capture the flow through fraction of load and post-load-wash phase. All these lines are processed in parallel on continuous chromatography system such as BioSMB (Pall), AKTA pcc (GE Healthcare), BioSC (Novasep), Contichrom (ChromaCon), etc. In at least one embodiment of the present disclosure, the harvested materials from the ATF device are subjected to a continuous product capture process using three columns, e.g., with 1.1/5 cm (inner diameter/bed height), packed with MABSELECT™ PRISM™ resin. In the load phase and post-load wash phase, two columns are connected in tandem, while in other phases, only one single column is processed. These two flowpaths are processed in parallel on BioSMB PD system and switched among three columns automatically. The continuous direct product capture process is much more efficient than traditional batch process.

VI. Examples

The present disclosure, thus generally described, will be understood more readily by reference to the following Examples, which are provided by way of illustration and are not intended to be limiting of the present disclosure.

A. Cell Lines and Culture Conditions

For Clone X: CHO-K1 host cell was purchased from ATCC (ATCC No.: CCL 61), and the vial was thawed and 100 vials of a master cell bank (MCB) were generated followed by generation of 136 vials of a working cell bank (WCB). Then the WCB vial was thawed and adapted into suspension culture with serum free media. 60 vials of PCB, 170 vials of MCB and 230 vials of WCB were generated with the suspension adapted clone CHO-K1-A4. One WCB vial of the CHO-K1 host cell CHO-K1-A4) was thawed for stable transfection.

The cDNA sequence to express an anti-hTNFα as disclosed in U.S. Pat. No. 6,090,382 was cloned into two vectors, which contained Blasticidin and Zeocin resistance markers, respectively. Stable transfection was performed using liposome. After transfection, cells were passaged in selective media (CD CHO media containing 9 μg/mL Blasticidin and 400 μg/mL Zeocin) for pool selection. After about 2 weeks of pool selection, the pools were cloned by FACS sorting. The clones were screened by fed-batch cultures in spin tubes. One high-producing clone, named Clone X, was selected.

For Clone Y: CHO-K1 host cell was purchased from ATCC (ATCC No.: CCL 61), and the vial was thawed and 100 vials of MCB were generated followed by generation of 136 vials of WCB. Then the WCB vial was thawed and adapted into suspension culture with serum free media. 60 vials of PCB, 170 vials of MCB and 230 vials of WCB were generated with the suspension adapted clone CHO-K1-A4. One WCB vial of the CHO-K1 host cell CHO-K1-A4) was thawed for stable transfection.

The cDNA sequence to express a fusion protein targeting VEGF as disclosed in U.S. Pat. No. 7,070,959B1 was cloned into two vectors, which contained Blasticidin and Zeocin resistance markers, respectively. Stable transfection was performed using liposome. After transfection, cells were plated in 96-well plates in selective media (CD CHO media containing 9 μg/mL Blasticidin and 400 μg/mL Zeocin) for minipool selection. After about 2 weeks of minipool selection, the high-producing minipools were expanded and mixed. The mixed minipools were cloned by two rounds of ClonePix, and the clones were screened by fed-batch cultures in spin tubes. One high-producing clone, named Clone Y, was selected.

For Clone Z: CHO-K1 host cell was purchased from ATCC (ATCC No.: CCL 61), and the vial was thawed and 100 vials of MCB were generated followed by generation of 136 vials of WCB. Then the WCB vial was thawed and adapted into suspension culture with serum free media. 60 vials of PCB, 170 vials of MCB and 230 vials of WCB were generated with the suspension adapted clone CHO-K1-A4. One WCB vial of the CHO-K1 host cell CHO-K1-A4) was thawed for stable transfection.

The cDNA sequence to express a bi-specific anti-CD3×CD19 antibody as disclosed in WO 2019/057124A1 was cloned into two vectors, which contained Blasticidin and Zeocin resistance markers, respectively. Stable transfection was performed using liposome. After transfection, cells were plated in 96-well plates in selective media (CD CHO media containing 9 μg/mL Blasticidin and 400 μg/mL Zeocin) for minipool selection. After about 2 weeks of minipool selection, the high-producing minipools were expanded individually. The minipools were cloned by one round of FACS, the clones were screened by fed-batch cultures in spin tubes. One high-producing clone, named Clone Z, was selected.

B. Example 1

In this example, using clone X, the performance of the intensified perfusion culture process (B) was directly compared to that of a traditional fed-batch process (A) and a concentrated fed-batch process (C).

Traditional Fed-Batch Process A:

Process A was executed in shake flasks. The traditional fed-batch process A was executed at 50 mL initial working volume in 250 mL vessel volume. Cells were inoculated at $0.40\times10^6$ cells/mL in CDM4 medium (Hyclone Laboratories Inc.) supplemented with 4.0 mM L-glutamine and subsequently cultured for 14 days. During culture, 3.00% basal medium CB7a and 0.30% feed medium CB7b were fed separately on Day 3, Day 6, Day 8 and Day 10. Temperature was shifted from 36.5° C. to 31.0° C. on Day 5. Glucose concentration was kept above 4.0 g/L by feeding 400 g/kg glucose stock solution during the whole culture process.

Intensified Perfusion Culture Process B:

Process B was performed in a 3 L APPLIKON™ vessel using delta V controller to control temperature at 36.5° C., at a pH range of about between 7.2 and 6.8 and at DO at 40% air saturation. A 0.2 μm cut-off hollow fiber filtration (Spectrum labs) operated in ATF flow mode with an ATF-2H system (Refine Technology) was used to retain the cells.

The culture was started with $0.80\text{-}1.00\times10^6$ cells/mL in CDM4 medium (Hyclone Laboratories Inc.) supplemented with 4.0 mM L-Glutamine. About 10-100 ppm of antifoam was added every day starting on Day 3. Perfusion of basal medium (CDM4, Hyclone Laboratories Inc.) was started from Day 1 with rate of 0.4 VVD was increased to 1.5 VVD on Day 3. Perfusion of feed medium (CB7a/CB7b) was started from Day 4 at rate of 2.0% of basal medium and increased to 4.0% of basal medium on Day 7. From Day 8, the perfusion rate of feed medium decreased gradually to 1% on Day 17 because of drop of cell density and viability.

From Day 3 until end of the culture, perfusion rate of CDM4 medium was kept at 1.5 VVD. A microsparger was used to deliver oxygen at a flow rate of 0.5 VVM. Temperature was shifted from 36.5° C. to 31.0° C. on Day 5 and kept at 31.0° C. until culture termination. The cell culture was continuously harvest through ATF. During the entire culture process, cells were retained in the bioreactor without bleeding.

Concentrated Fed-Batch Process C:

Process C was performed using delta V controller to control temperature at 36.5° C., at a pH range of about between 7.2 and 6.8 and at DO at 40% air saturation. The operations of concentrated fed batch process were consistent with process B, except the cut-off hollow fiber filtration (Spectrum labs), whose pore was 50 KD to retain both the cell and the biological product in the culture broth.

Figure 2:
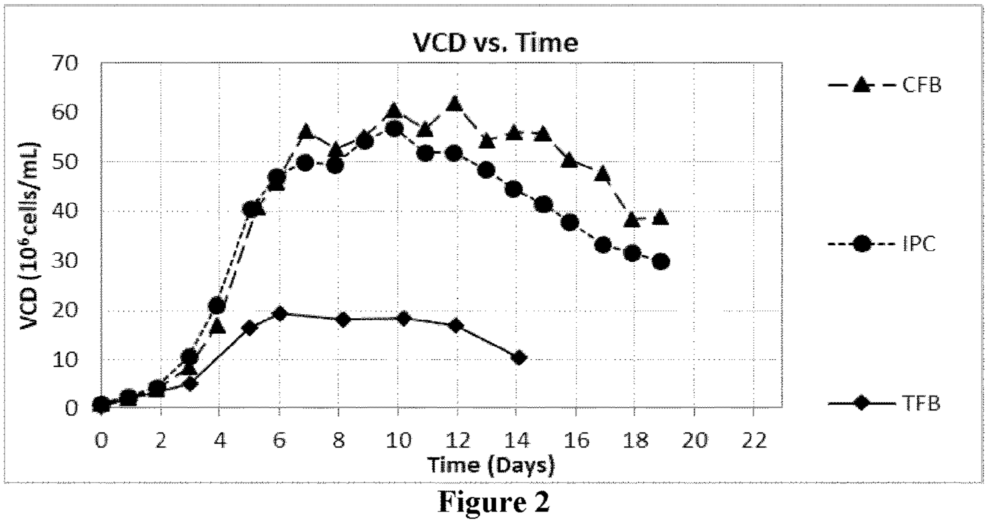
FIG. 2 shows the viable cell density ($10^6$/mL) plotted versus the process time (days) for process A (traditional Fed-batch), process B (intensified perfusion culture) and process C (concentrated fed-batch) in Example 1.

Comparison Between the Processes:

FIG. 2 shows that higher peak viable cell density is achieved in process B and C, almost tripled when compared with the traditional fed-batch process A.

Figure 3:
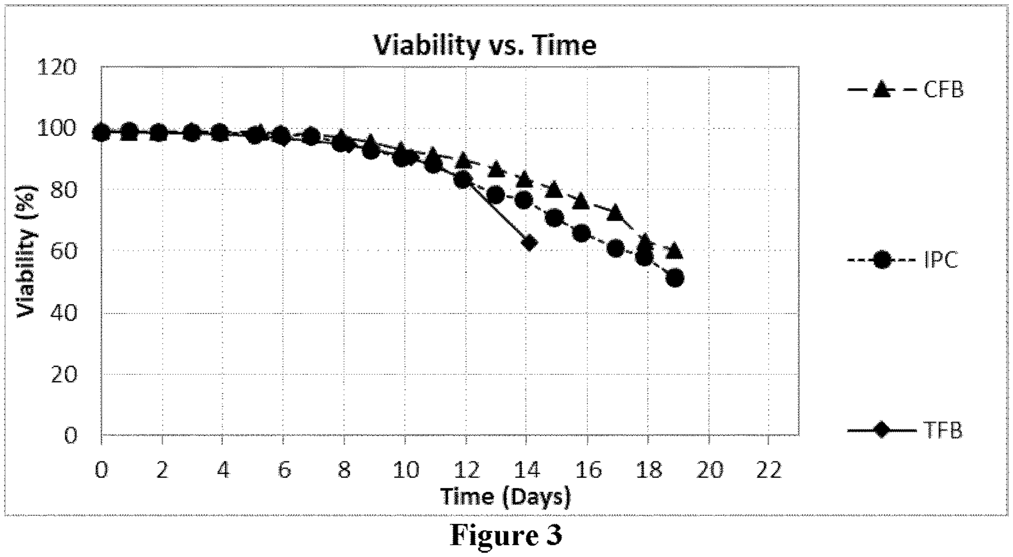
FIG. 3 shows the viability (%) plotted versus the process time (days) for process A (traditional Fed-batch), process B (intensified perfusion culture) and process C (concentrated fed-batch) in Example 1.

FIG. 3 shows that the viability of the cells can be maintained longer with process B and C, as process B and process C were maintained in operation over a period of 19 days.

Figure 4:
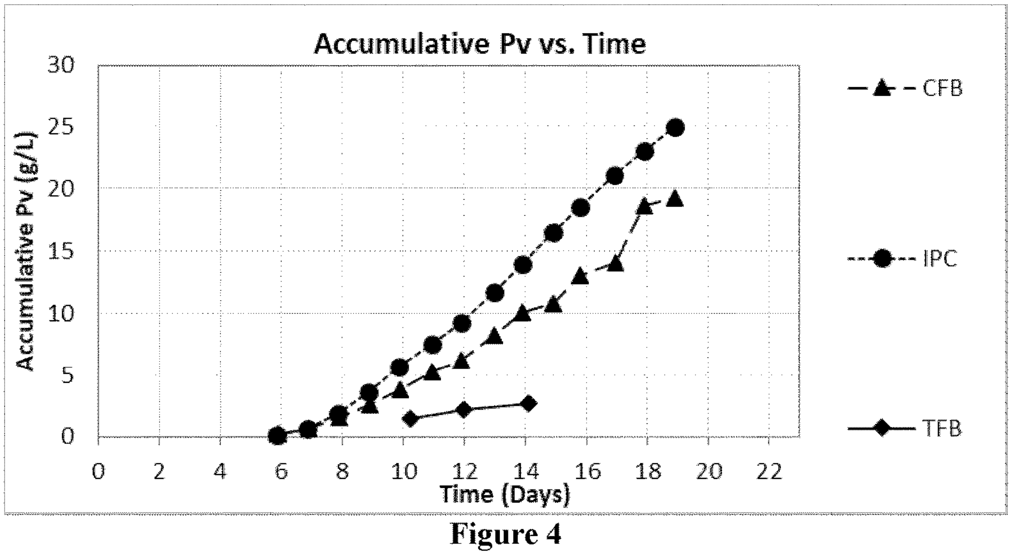
FIG. 4 shows the accumulative volumetric productivity (Pv) (g/L) plotted versus the process time (days) for process A (traditional Fed-batch), process B (intensified perfusion culture) and process C (concentrated fed-batch) in Example 1.

FIG. 4 shows that accumulative Pv from the process B are the highest when compared with process A and process C. Accumulative Pv from process B is approximately 9.41 times and 1.29 times higher than the final concentration in the traditional fed-batch process A and concentrated fed batch process C separately. The final concentration in concentrated fed batch process C here is adjusted by packed cell volume.

Figure 5:
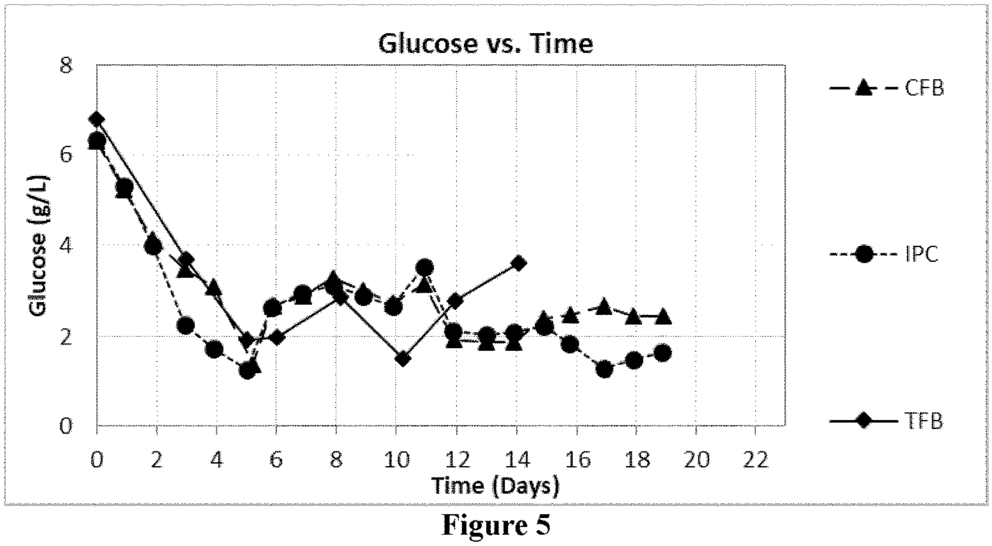
FIG. 5 shows the glucose concentration for process A (traditional Fed-batch), process B (intensified perfusion culture) and process C (concentrated fed-batch) in Example 1.

FIG. 5 shows that smoother glucose concentration control is achieved in process B and concentrated fed batch process C compared with traditional fed-batch process A.

Figure 6:
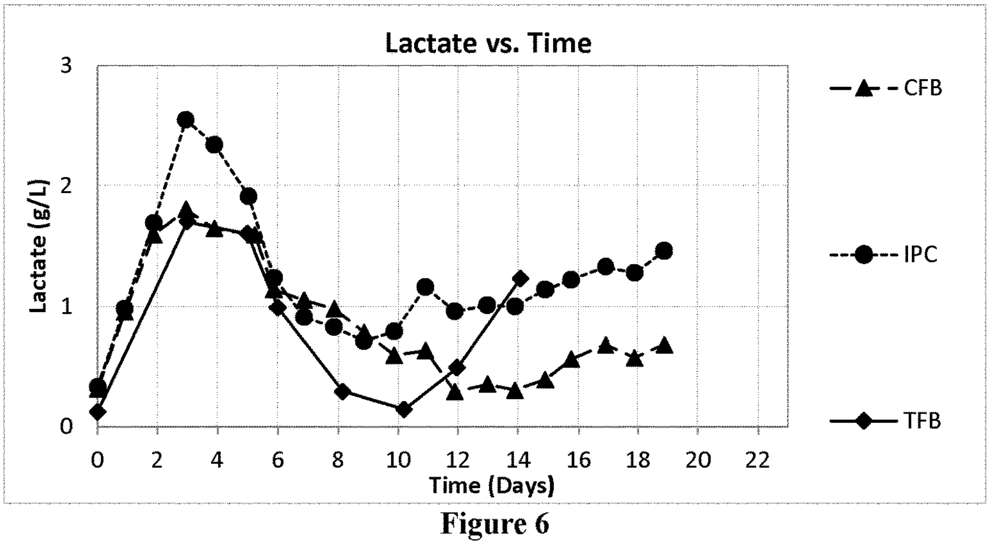
FIG. 6 shows the lactate production or accumulation for process A (traditional Fed-batch), process B (intensified perfusion culture) and process C (concentrated fed-batch) in Example 1.

FIG. 6 shows that no obvious lactate production or accumulation problem is observed in process B and process C, while lactate concentration in process A showed an upward trend from day 10.

Figure 7:
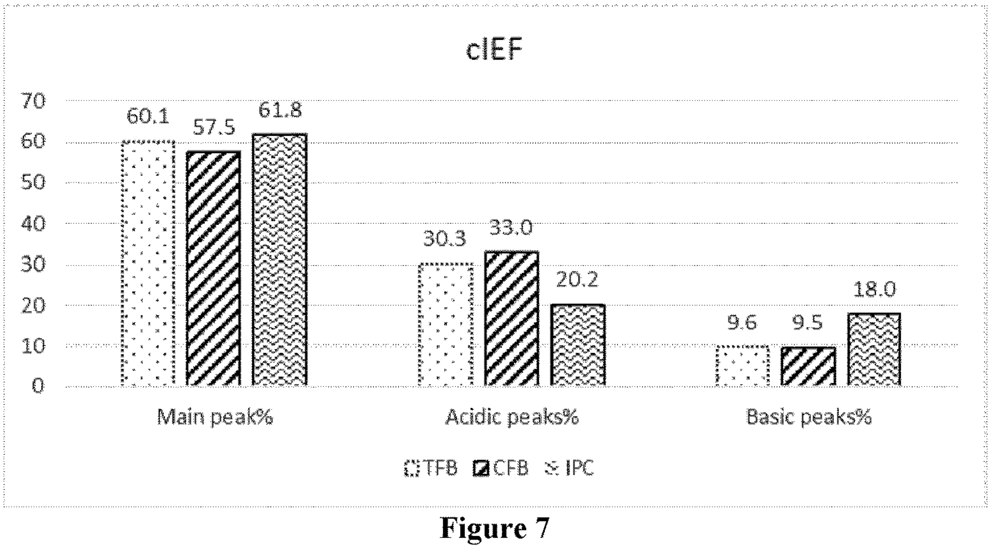
FIG. 7 shows the cIEF (Capillary Isoelectric Focusing) results for process A (traditional Fed-batch), process B (intensified perfusion culture) and process C (concentrated fed-batch) in Example 1.

FIG. 7 shows that increased cIEF main peaks along with reduction of the acidic peaks is achieved in process B compared with process A and process C.

Figure 8:
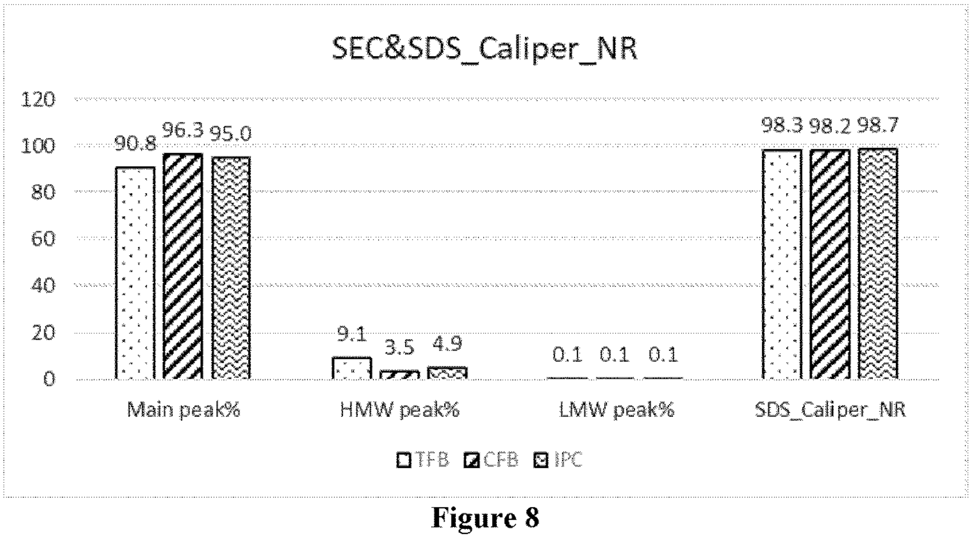
FIG. 8 shows the SEC and SDS_caliper_NR results for process A (traditional Fed-batch), process B (intensified perfusion culture) and process C (concentrated fed-batch) in Example 1.

FIG. 8 shows comparisons of the aggregates and fragments produced by the process B and the other two processes A, C. SEC main peak from the process B is comparable to concentrated fed batch process C and both of them are higher than traditional fed-batch process A. Purity of SDS_Caliper_NR from the process B has no obvious differences when compared with process A and process C.

The harvested material from process B was collected from day 9 to day 21, and stored in three bags for Day 9 to Day 13, Day 13 to Day 17, and Day 17 to Day 21, respectively. For each harvest pool, about 100 mL sample was taken for the batch mode evaluation on small column, and the remainder was processed by BioSMB system in continuous mode. The yield and productivity of traditional batch and continuous process were compared, meanwhile the product quality attributes, SEC purity and HCP content, were also evaluated.

Traditional Batch Direct Product Capture Process:

The batch mode chromatography was performed on AKTA pure system with a 0.5/5.6 cm (inner diameter/bed height) column packed with MABSELECT™ PRISM™ resin. Table 1 shows the process parameters of each step in the chromatography.

The loading capacity was 65 g/L resin, and the residence time for loading was 5 minutes. The chromatography step was done at room temperature (18° C. to 26° C.). The load volume was determined by the volume totalizer of chromatography system, while the elution pool volume was determined by the net weight of collected sample. The yield was calculated based on the product amount in elution pool divided by the product amount in loading pool. The concentration of elution pool was determined by UV absorbance at 280 nm wavelength, while the concentration of loading pool was determined by Protein A HPLC. The productivity was calculated based on the processed product amount divided by the process time and the volume of resin.

The elution pool was neutralized to pH5.5, and then filtrated with 0.2 μm PES syringe filter after elution. The SEC purity and HCP content of the neutralized pool were determined by SEC HPLC and commercial ELISA kit for CHO cells, respectively.

Continuous Direct Product Capture Process:

The continuous mode chromatography was performed on BioSMB PD system with three 1.1/5 cm (inner diameter/bed height) columns packed with MABSELECT™ PRISM™ resin. Table 3 shows the detailed process parameters of each step in the chromatography. In the load phase and post-load wash phase, two columns were connected in tandem, while in the other phases, only one single column was processed. These two flowpaths were processed in parallel on BioSMB PD system and switched among three columns automatically.

The loading capacity and residence time of continuous process were calculated based on the break through curves at different residence time and load concentration, and were different for the materials with different titer as shown in Table 4. The other operation conditions not specified were similar to those of batch process described above.

The yield, productivity, SEC purity, and HCP content of batch and continuous process were summarized as shown in Table 2 and Table 4, respectively. The consistent yield and product quality attributes data across culture time reveals that the variation of starting material from intensified perfusion culture process B has minor impact on the downstream process, and the continuous product capture process is comparable to batch process. The 77% higher productivity indicates that continuous direct product capture process can significantly improve the productivity of capture step comparing to traditional batch process. The intensified perfusion culture process B is considered stable, and the continuous direct product capture process is much more efficient than traditional batch process.

TABLE 2

Batch Model Process Summary

| Harvest Time (Day) | Load Capacity (mg/mL resin) | Load Concentration (mg/mL) | Residence Time of Load (min) | SEC Purity (%) Monomer | HMW | LMW | HCP Content (ppm) | Yield (%) | Productivity (g/L/h) | Overall Productivity (g/L/h) |
|---|---|---|---|---|---|---|---|---|---|---|
| 9-13 | 65 | 1.17 | 5 | 91.5 | 8.5 | <0.1 | 497 | 88.12 | 12.14 | 13.74 |
| 13-17 | | 1.57 | | 92.0 | 7.9 | 0.1 | 674 | 90.75 | 15.26 | |
| 17-21 | | 1.39 | | 93.1 | 6.9 | 0.1 | 659 | 87.87 | 14.19 | |

TABLE 1

Process Parameters of Batch Mode Chromatography

| Step | Buffer | pH | Conductivity (mS/cm) | Flow Rate (mL/min) | Volume (CV) |
|---|---|---|---|---|---|
| Rinse 1 | 50 mM Tris-HAc, 150 mM NaCl, pH 7.4 | 7.53 | 17.00 | 1.10 | 2 |

TABLE 1-continued

Process Parameters of Batch Mode Chromatography

| Step | Buffer | pH | Conductivity (mS/cm) | Flow Rate (mL/min) | Volume (CV) |
|---|---|---|---|---|---|
| Pre-use Sanitization | 0.1M NaOH | NA | NA | 1.10 | 5 |
| Equilibration | 50 mM Tris-HAc, 150 mM NaCl, pH 7.4 | 7.53 | 17.00 | 1.10 | 5 |
| Load | NA | NA | NA | 0.22 | NA |
| Wash 1 | 50 mM Tris-HAc, 150 mM NaCl, pH 7.4 | 7.53 | 16.998 | 1.10 | 6 |
| Wash 2 | 50 mM NaAc-HAc, 1M NaCl, pH5.5 | 5.52 | 89.264 | 1.10 | 3 |
| Wash 3 | 50 mM NaAc-HAc, pH5.5 | 5.6 | 3.474 | 1.10 | 5 |
| Elution | 50 mM NaAc-Hac, pH3.8 | 3.81 | 0.528 | 0.49 | 6 |
| Strip | 1M HAc | NA | NA | 1.099 | 3 |
| Rinse 2 | 50 mM Tris-HAc, 150 mM NaCl, pH 7.4 | 7.53 | 16.998 | 1.099 | 2 |
| Post-use Sanitization | 0.1M NaOH | NA | NA | 1.099 | 5 |
| Rinse 3 | 50 mM Tris-HAc, 150 mM NaCl, pH 7.4 | 7.53 | 16.998 | 1.099 | 2 |

TABLE 3

Process Parameters of Continuous Mode Chromatography

| Step | Buffer | pH | Conductivity (mS/cm) | Flow Rate (mL/min) | Volume (CV) |
|---|---|---|---|---|---|
| Equilibration | 50 mM Tris-HAc, 150 mM NaCl, pH 7.4 | 7.50 | 16.888 | 4.8 | 5 |
| Load | NA | NA | NA | NA | NA |
| Post-Load Wash | 50 mM NaAc-HAc, 1M NaCl, pH5.5 | 5.52 | 89.264 | NA | 3 |
| Wash 1 | 50 mM Tris-HAc, 150 mM NaCl, pH 7.4 | 7.50 | 16.888 | 4.8 | 3 |
| Wash 2 | 50 mM NaAc-HAc, 1M NaCl, pH5.5 | 5.52 | 89.264 | 4.8 | 3 |
| Wash 3 | 50 mM NaAc-HAc, pH5.5 | 5.60 | 3.474 | 4.8 | 5 |
| Elution | 50 mM NaAc-Hac, pH3.8 | 3.81 | 0.528 | 4.8 | 7.5 |

TABLE 3-continued

| Process Parameters of Continuous Mode Chromatography | | | | | |
|---|---|---|---|---|---|
| Step | Buffer | pH | Conductivity (mS/cm) | Flow Rate (mL/min) | Volume (CV) |
| Strip | 1M HAc | NA | NA | 4.8 | 3 |
| Rinse 2 | 50 mM Tris-HAc, 150 mM NaCl, pH 7.4 | 7.50 | 16.888 | 4.8 | 2 |
| Post-use Sanitization | 0.1M NaOH | NA | NA | 4.8 | 3 |

0.4 VVD and the rate was increased to 1.5 VVD on Day 3. In experiments IPC-1 through IPC-5, the perfusion rate of CDM4 medium was kept at 1.0 VVD from day 5 until end of the culture. In experiments IPC-6 through IPC-8, the perfusion rate of CDM4 medium was kept at 1.5 VVD from day 5 until end of the culture.

In experiments IPC-1, IPC-2, IPC-3, IPC-4, IPC-5, IPC-6, and IPC-8, the temperature was shifted from about 36.5° C. to about 31.0° C. on Day 6 and kept at about 31.0° C. until culture the end of the culture. In experiments IPC-7, the temperature was shifted from about 36.5° C. to about 33.0° C. on Day 6 and kept at about 33.0° C. until the end of the culture.

TABLE 4

Continuous Model Process Summary

| Harvest Time (Day) | Load Capacity (mg/mL resin) | Load Concentration (mg/mL) | Residence Time of Load and Post Load Wash (min) | Cycle # of Resin | SEC Purity (%) Monomer | HMW | LMW | HCP Content (ppm) | Yield (%) | Productivity (g/L/h) | Overall Productivity (g/L/h) | Productivity Increase (% of Batch Process) |
|---|---|---|---|---|---|---|---|---|---|---|---|---|
| 9-13 | 76 | 1.17 | 1 | 1-15 | 91.7 | 8.3 | <0.1 | 925 | 92.70 | 20.47 | 24.36 | 77 |
| 13-17 | 79 | 1.57 | 1 | 16-35 | 91.0 | 8.9 | 0.1 | 1211 | 89.64 | 28.49 | | |
| 17-21 | 78 | 1.39 | 1 | 36-52 | 92.8 | 7.1 | 0.1 | 643 | 89.53 | 24.26 | | |

C. Example 2

In this example, using clone X, the performance of the intensified perfusion culture process (B) was evaluated.

Intensified Perfusion Culture Process

Experiments IPC-1 through IPC-8 were performed using a delta V controller to control temperature at about 36.5° C., at a pH range of about between 7.2 and 6.8 and at a DO at about 40% air saturation. A 0.2 μm cut-off hollow fiber filtration (Spectrum labs) for all processes (except process 5 whose pore of cut-off hollow fiber filtration was 0.45 μm) operated in ATF flow mode with an ATF-2H system (Refine Technology) was used to retain the cells.

Experiments IPC-1, IPC-2, and IPC-3 were performed in 7 L APPLIKON™ vessel and experiments IPC-4, IPC-5, IPC-6, IPC-7, and IPC-8 were performed in 3 L APPLIKON™ vessel.

The cultures for experiments IPC-1 through IPC-8 were started with about 0.90-1.10×$10^6$ cells/mL in CDM4 medium (Hyclone Laboratories Inc.) supplemented with 4.0 mM L-Glutamine and about 10-100 ppm antifoam was added every day from Day 0.

In experiments IPC-1, IPC-4, and IPC-5, the perfusion of basal medium (CDM4, Hyclone Laboratories Inc.) started on Day 2 with rate of 0.4 VVD and the rate was increased to 1.0 VVD on Day 4. In experiments IPC-2, and IPC-3, the perfusion of basal medium (CDM4, Hyclone Laboratories Inc.) started from Day 1 with rate of 0.4 VVD and the rate was increased to 1.0 VVD on Day 2. In experiments IPC-6, the perfusion of basal medium (CDM4, Hyclone Laboratories Inc.) started from Day 2 with rate of 0.4 VVD and the rate was increased to 1.5 VVD on Day 4. In experiments IPC-7, and IPC-8, the perfusion of basal medium (CDM4, Hyclone Laboratories Inc.) started from Day 1 with rate of In experiments IPC-1 through IPC-8, the perfusion of feed medium (CB7a/CB7b) started from Day 3 and its rate was adjusted daily according to the previous day's glucose utilization to keep glucose concentration above 2.0 g/L with the lowest feeding rate. A microsparger was used to deliver oxygen at a flow rate of 0.5 VVM. Cell culture was continuously harvest through ATF. During the whole culture process, cells were retained in the bioreactor without bleeding.

Figure 9:
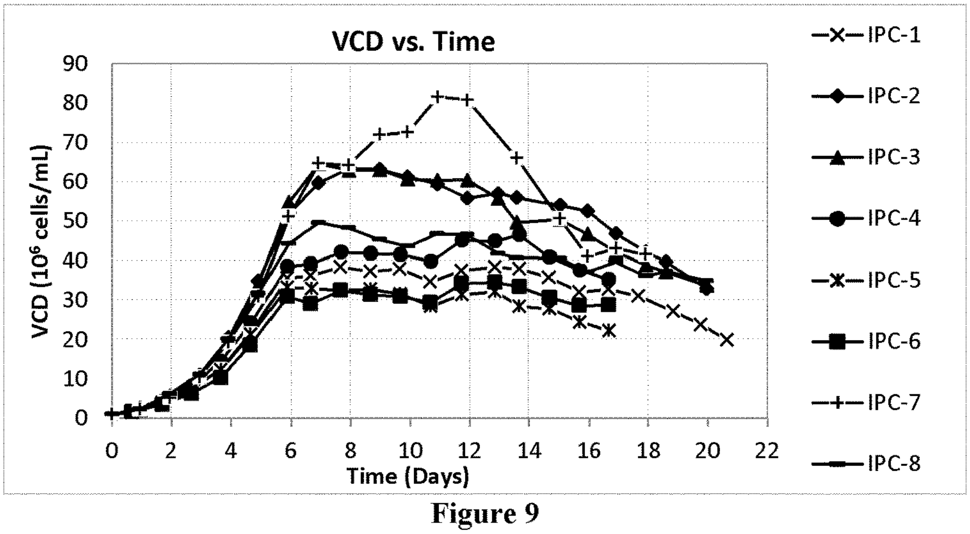
FIG. 9 shows the viable cell density ($10^6$/mL) plotted versus the process time (days) for the experiments IPC-1 through IPC-8 in Example 2.

FIG. 9 shows that all processes achieve high peak viable cell density (above 30×$10^6$ cells/mL) and can maintain at the high level for 5-6 days except process 7, whose temperature was kept at 33.0° C. after Day 6.

Figure 10:
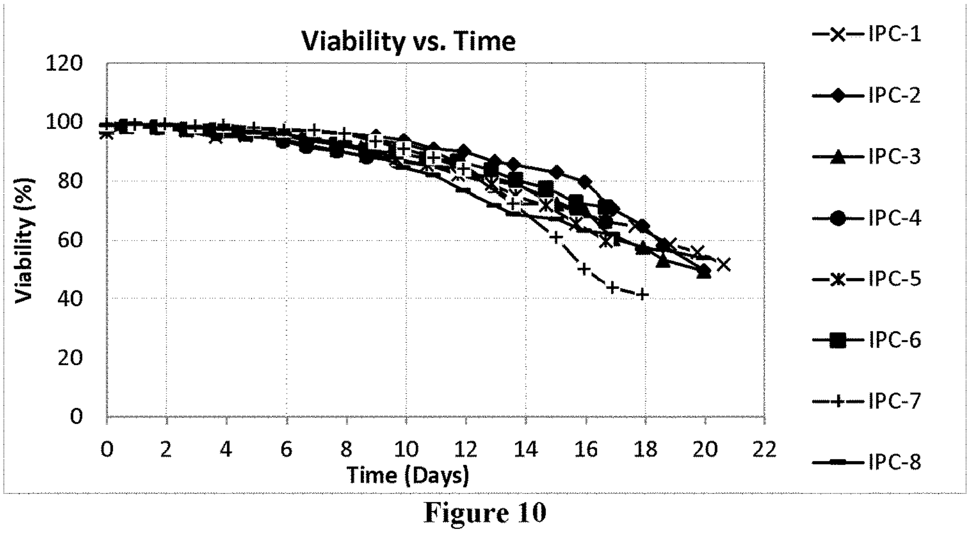
FIG. 10 shows that the viability of the cells in for the experiments IPC-1 through IPC-8 in Example 2.

FIG. 10 shows that the viability of the cells in all processes can be maintained above 50% throughout the cultivation for nearly 20 days, except process 7, whose end-point viability is 40%.

Figure 11:
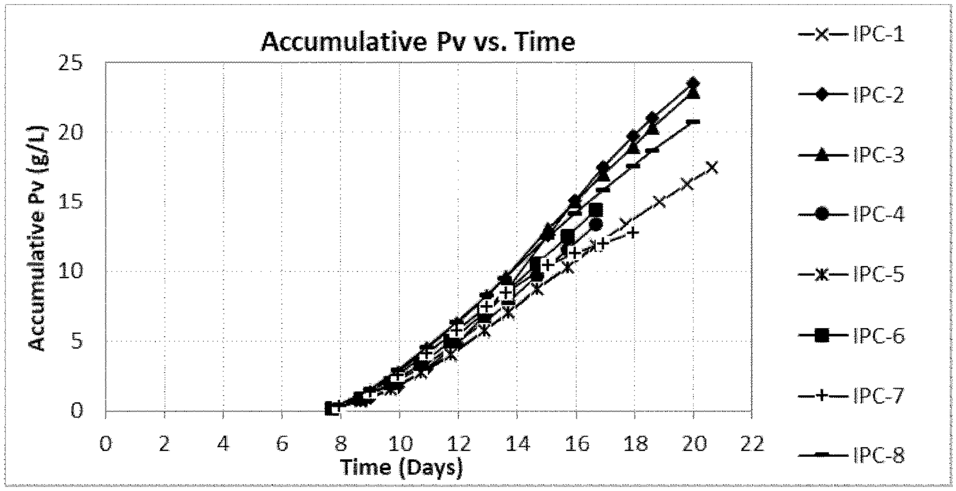
FIG. 11 shows that accumulative volumetric productivity (Pv) for the experiments IPC-1 through IPC-8 in Example 2.

FIG. 11 shows that accumulative volumetric productivity (Pv) from all processes is above 12 g/L and the highest is 23 g/L.

Figure 12:
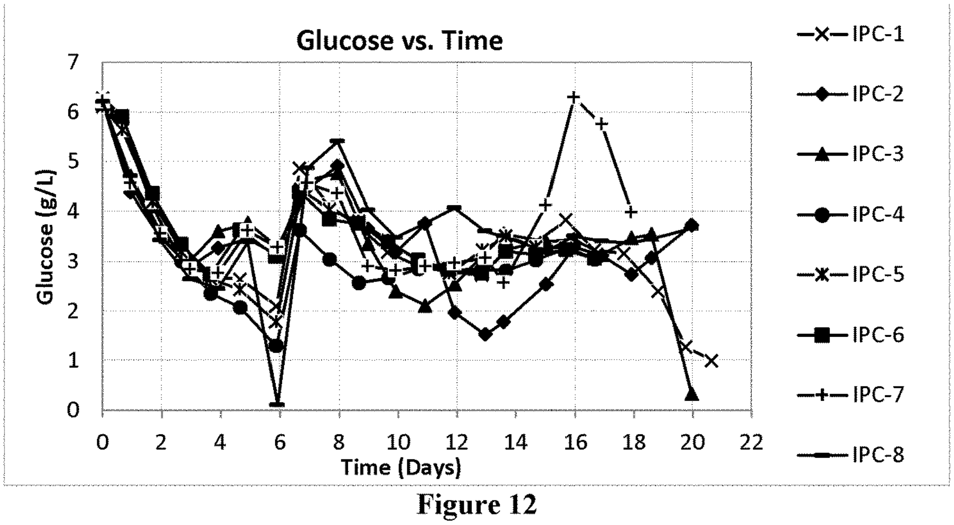
FIG. 12 shows the glucose concentration of the experiments IPC-1 through IPC-8 in Example 2.

FIG. 12 shows that glucose concentration of most processes is controlled above 2 g/L for the whole culture duration.

Figure 13:
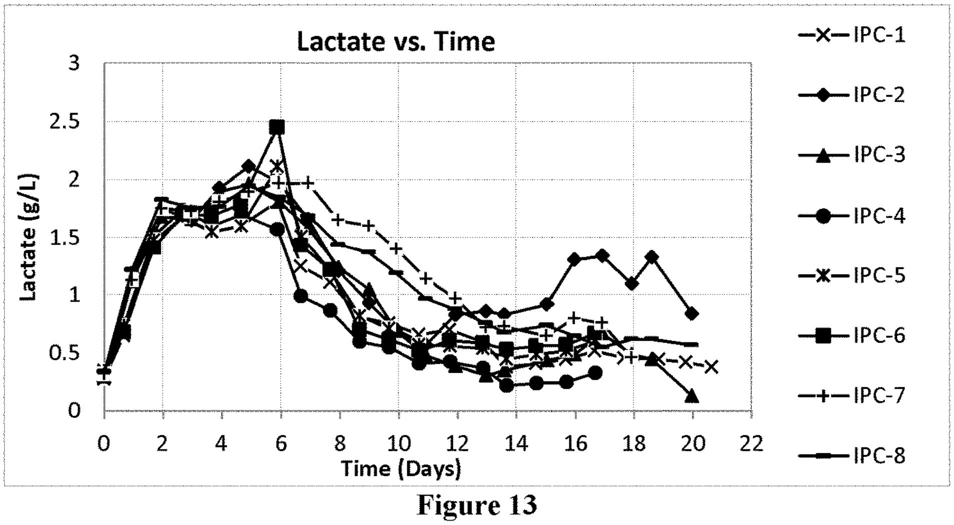
FIG. 13 shows the lactate concentration for the experiments IPC-1 through IPC-8 in Example 2.

FIG. 13 shows that a typical lactate production period during the exponential growth phase followed by the lactate consumption is observed in all processes.

D. Example 3

In this example, using clone Y, the performance of the intensified perfusion culture process (B) was directly compared to that of a traditional fed-batch process (A) and a perfusion process (C).

Traditional Fed-Batch Process A:

Process A was executed in shake flask at 50 mL initial working volume in 250 mL vessel volume. Cells were inoculated at 0.40×$10^6$ cells/mL in Excell Advanced CHO medium (Sigma) supplemented with 6 mM L-glutamine and subsequently cultured for 14 days. During culture, 3.00% basal medium CB7a and 0.30% feed medium CB7b were fed separately on Day 3, Day 6, Day 8 and Day 10. Temperature was shifted from 36.5° C. to 33.0° C. on Day 5. Glucose concentration was kept above 2.0 g/L by feeding 400 g/kg glucose stock solution.

Intensified Perfusion Culture Process B

Process B was performed using a delta V controller to control temperature at about 36.5° C., at a pH range of about between 7.2 and 6.8 and at a DO at about 40% air saturation. Process B was performed in a 3 L APPLIKON™ vessel with a 0.2 μm cut-off hollow fiber filtration (Spectrum labs) operated in ATF flow mode with an ATF-2H system (Refine Technology) was used to retain the cells. The culture was started with 0.70-0.80×$10^6$ cells/mL in Excell Advanced CHO medium (Sigma) supplemented with 6.0 mM L-glutamine. About 10 to 100 ppm antifoam was added every day starting on Day 5 until the end of the culture process. Perfusion of basal medium (Excell Advanced CHO medium, Sigma) was started from Day 1 with rate of 0.4 VVD and the rate was increased to 1.5 VVD on Day 4. Perfusion of feed medium (CB7a/CB7b) was started from Day 5 at rate of 2.0% of basal medium and increased to 9.0% of basal medium on Day 12. On Day 18, the perfusion rate of feed medium decreased to 7% and maintained at 6% from Day 19 until the end of the culture. From Day 4 until end of the culture, perfusion rate of basal medium was kept at 1.5 VVD. A microsparger was used to deliver oxygen at a flow rate of 0.5 VVM. The temperature was shifted from about 36.5° C. to about 33.0° C. on Day 5 and kept at 33.0° C. until culture termination. Cell culture was continuously harvest through ATF. During the whole culture process, cells were retained in the bioreactor without bleeding.

Perfusion Cell Culture Process C:

Perfusion process C was explored using delta V controller to control temperature at 34.5° C., pH between 7.1 and 6.7 and DO at 40% air saturation. Process C was performed in a 7 L APPLIKON™ vessel with a 0.2 μm cut-off hollow fiber filtration (Spectrum labs) operated in ATF flow mode with an ATF-2H system (Refine Technology) was used to retain the cells. The culture was started with about 0.50-0.60×$10^6$ cells/mL in Excell Advanced CHO medium (Sigma) supplemented with 6.0 mM L-glutamine and an additional 2.5 g/L glucose. About 10-100 ppm antifoam was added every day from Day 4. Perfusion of basal medium (Excell Advanced CHO medium, Sigma) was started from Day 2 with rate of 0.5 VVD and the rate was increased to 1.5 VVD on Day 5. Perfusion of feed medium (CB7a/CB7b) was started from Day 37 at rate of 2.0% of basal medium and kept this rate until culture termination. From Day 5 until end of the culture, perfusion rate of basal medium was kept at 1.5 VVD. A microsparger was used to deliver oxygen at a flow rate of 0.5 VVM. Temperature was set at 34.5° C. during the whole culture process. Cell culture was continuously harvest through ATF. During the whole culture process, VCD was targeted at 50.00×$10^6$ cells/mL by bleeding to remove the excessive cells.

Figure 14:
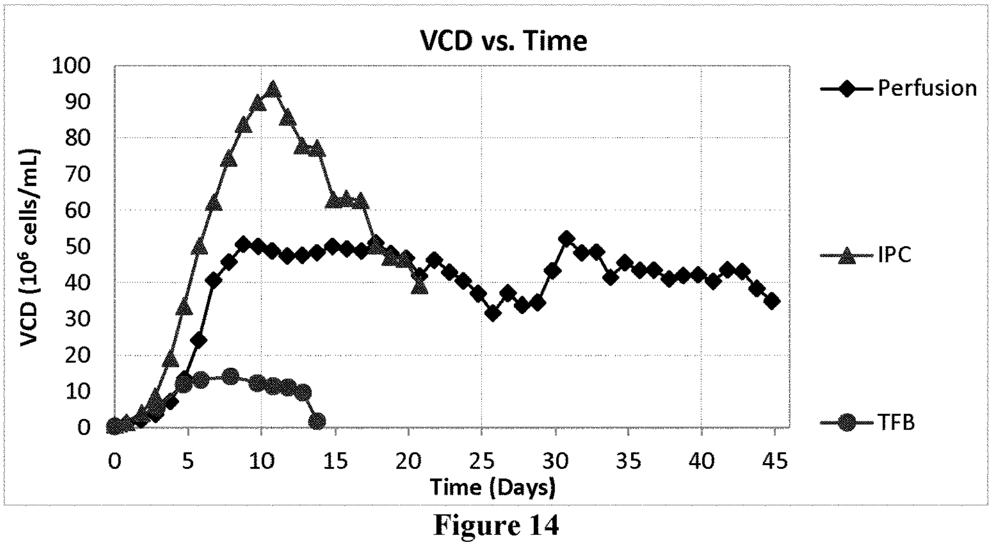
FIG. 14 shows the viable cell density ($10^6$/mL) plotted versus the process time (days) for process A (traditional Fed-batch), process B (intensified perfusion culture) and process C (perfusion cell culture) in Example 3.

FIG. 14 shows that higher peak viable cell density is achieved in process B, almost sevenfold when compared with the traditional fed-batch process A. Process B can obtain more biomass compared with the perfusion process C during the same culture period.

Figure 15:
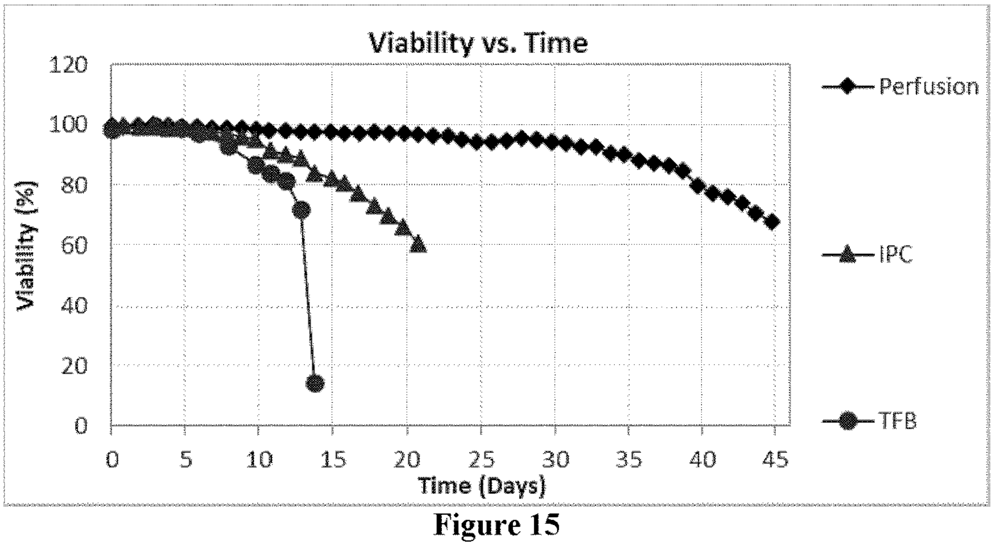
FIG. 15 shows the viability (%) plotted versus the process time (days) for process A (traditional Fed-batch), process B (intensified perfusion culture) and process C (perfusion cell culture) in Example 3.

FIG. 15 shows that the process B can maintain a higher viability for a longer duration of 21 days when compared to the traditional fed-batch process A with a 14 days duration.

Figure 16:
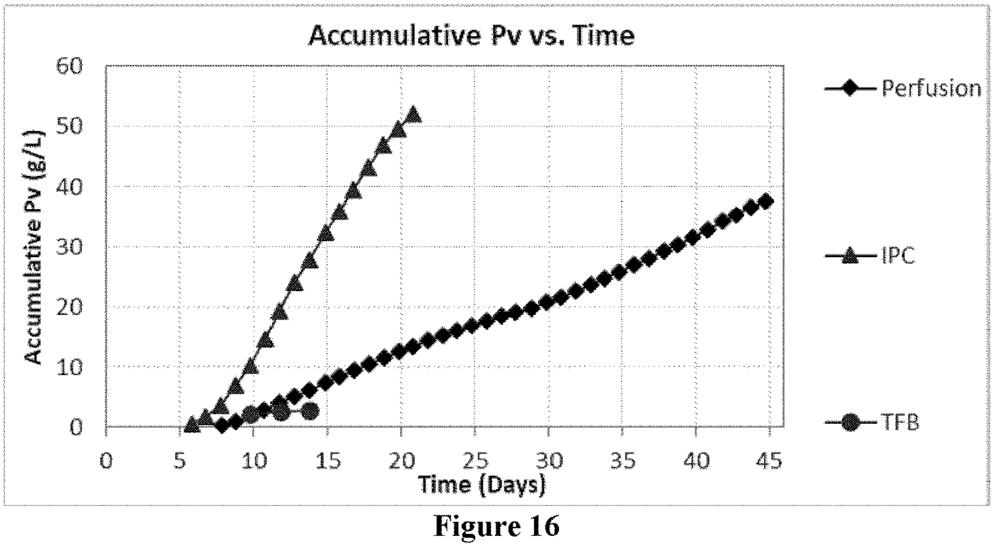
FIG. 16 shows the accumulative Pv (g/L) plotted versus the process time (days) for process A (traditional Fed-batch), process B (intensified perfusion culture) and process C (perfusion cell culture) in Example 3.

FIG. 16 shows that accumulative Pv from the process B is approximately 18.49 times and 1.39 times higher than the final concentration in process A and process C separately. Considering the capacity defined by the productivity per working volume per day, process B (2.48 g/L/day) is almost three times higher than perfusion process C (0.83 g/L/day).

Figure 17:
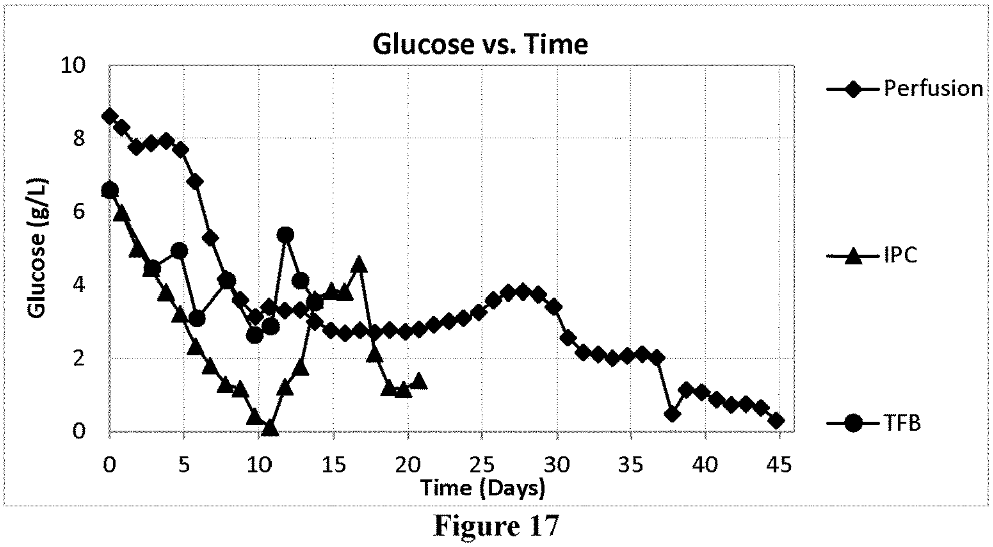
FIG. 17 shows the glucose concentration for process A (traditional Fed-batch), process B (intensified perfusion culture) and process C (perfusion cell culture) in Example 3.

FIG. 17 shows that different glucose profiles are presented in different processes with different glucose control strategy.

Figure 18:
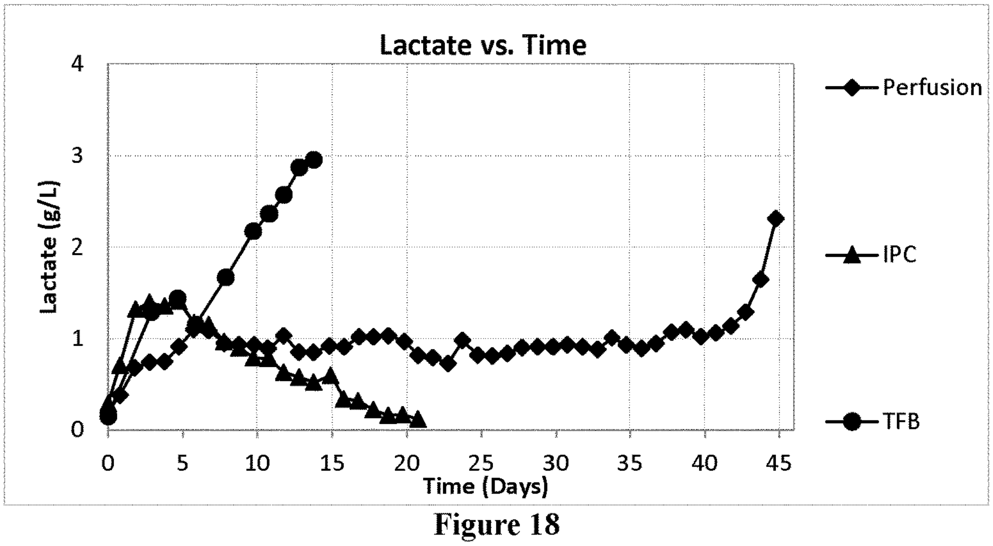
FIG. 18 shows the lactate production or accumulation for process A (traditional Fed-batch), process B (intensified perfusion culture) and process C (perfusion cell culture) in Example 3.

FIG. 18 shows that a typical lactate production period during the exponential growth phase followed by the lactate consumption is observed in process B compared with process A and C with rising lactate concentration in later stages of culture.

E. Example 4

In this example, using clone Z, the performance of the intensified perfusion culture process (B) was directly compared to that of a traditional fed-batch process (A).

Traditional Fed-Batch Process A:

The traditional fed-batch process was developed on a 3 L scale, and scaled up to 15 L. The traditional fed-batch process A was executed at 2.0 L initial working volume in a 3 L APPLIKON™ Vessel. Cells were inoculated at 0.60×$10^6$ cells/mL in specialized CHO culture medium ACTIPRO™ (Hyclone Laboratories Inc.) supplemented with 4 mM L-glutamine, 1% (v/v) hypoxanthine monosodium and 1% (v/v) thymidine and subsequently cultured for 14 days. During culture, 3.00%, 5.00%, 5.00% and 5.00% feed medium CB7a combined with 0.30%, 0.50%, 0.50% and 0.50% feed medium CB7b were fed separately on Day 3, Day 5, Day 7 and Day 10. Temperature was shifted from 36.5° C. to 31.0° C. on Day 5. Glucose concentration was kept above 1 g/L by feeding 400 g/kg glucose stock solution.

Intensified Perfusion Culture Process B:

Process B was developed in 3 L scale, and scaled up in 15 L and 250 L. For the 3 L scale process, 1.5 L working volume was cultured in 3 L APPLIKON™ vessel. For the 15 L scale process, 10 L working volume was cultured in 15 L APPLIKON™ vessel. For the 250 L scale, 150 L working volume was cultured in SUB 250 L single use bioreactor. 0.2 μm hollow fiber filtration (Spectrumlabs/Refine Technology) operated in ATF flow mode with an ATF system (Refine Technology) was used to retain the cells. Process B was performed using delta V controller to control temperature at about 36.5° C., at a pH range of about between 7.2 and 6.8 and at a DO at about 40% air saturation.

For the 3 L scale experiment, the culture was started with 1.10-1.30×106 cells/mL in specialized CHO culture medium ACTIPRO™ (Hyclone Laboratories Inc.) supplemented with 4 mM L-glutamine, 1% (v/v) hypoxanthine monosodium and 1% (v/v) thymidine. About 10-100 ppm antifoam was added everyday from Day 2. Perfusion of basal medium (specialized CHO culture medium ACTIPRO™, Hyclone Laboratories Inc.) was started from Day 2 with rate of 0.6 VVD and the rate was increased to 0.88 VVD on Day 6. Perfusion of feed medium CB7a was started from Day 2 at rate of 6.7% of basal medium and increased to 15.9% of basal medium. Perfusion of feed medium CB7b was started from Day 2 and kept the rate at 0.005 VVD until culture termination. From Day 6 till terminal of culture, perfusion rate of basal medium was kept at 0.88 VVD. A microsparger was used to deliver oxygen at a flow rate of 0.33 VVM. Temperature was shifted from 36.5° C. to 31.0° C. on Day 5 and kept at 31.0° C. until culture termination. Cell culture was continuously harvest through ATF. During the whole culture process, cells were retained in the bioreactor without bleeding.

For the 250 L scale experiment, the culture was started with 0.80-1.40×$10^6$ cells/mL in specialized CHO culture medium ACTIPRO™ (Hyclone Laboratories Inc.) supplemented with 4 mM L-glutamine, 1% (v/v) hypoxanthine monosodium and 1% (v/v) thymidine. About 10 to 100 ppm antifoam was added every day after Day 2. Perfusion of basal medium (specialized CHO culture medium ACTIPRO™, Hyclone Laboratories Inc.) was started from Day 2 with rate of 0.6 VVD and the rate was increased to 0.88 VVD on Day 6. Perfusion of feed medium CB7a was started from Day 2 at rate of 6.7% of basal medium and increased to 15.9% of basal medium. Perfusion of feed medium CB7b was started from Day 2 and kept the rate at 0.005 VVD until culture termination. From Day 6 till end of the culture, perfusion rate of basal medium was kept at 0.88 VVD. A microsparger was used to deliver oxygen from Day 4. Temperature was shifted from 36.5° C. to 31.0° C. on Day 5 and kept at 31.0° C. until the end of the culture. The cell culture was continuously harvest through ATF. During the whole culture process, cells were retained in the bioreactor without bleeding.

The same process was scaled up to 15 L bioreactor and 250 L bioreactor respectively. For the culture in 15 L bioreactor, 0.2 μm cut-off hollow fiber filtration (Spectrumlabs) operated in ATF flow mode with two ATF-2H systems (Refine Technology) was used to retain the cells. For the culture in 250 L bioreactor, 0.2 μm cut-off hollow fiber filtration (Spectrumlabs) operated in ATF flow mode with two ATF-6 systems (Refine Technology) was used to retain the cells.

Figure 19:
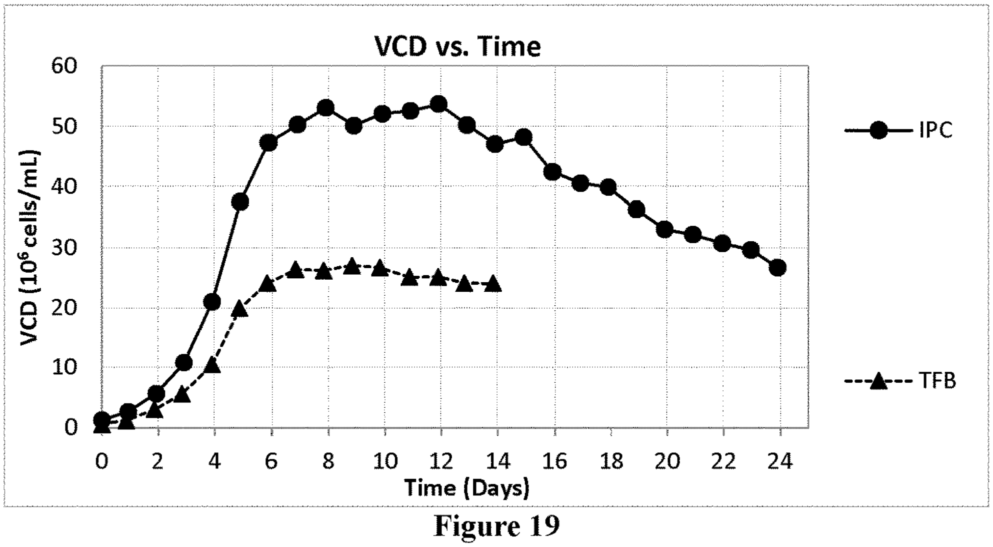
FIG. 19 shows the viable cell density ($10^6$/mL) plotted versus the process time (days) for processes A and B in Example 4.

FIG. 19 shows that longer exponential growth phase and almost twice higher peak viable cell density are demonstrated in process B when compared with the traditional fed-batch process A at the same 3 L scale.

Figure 20:
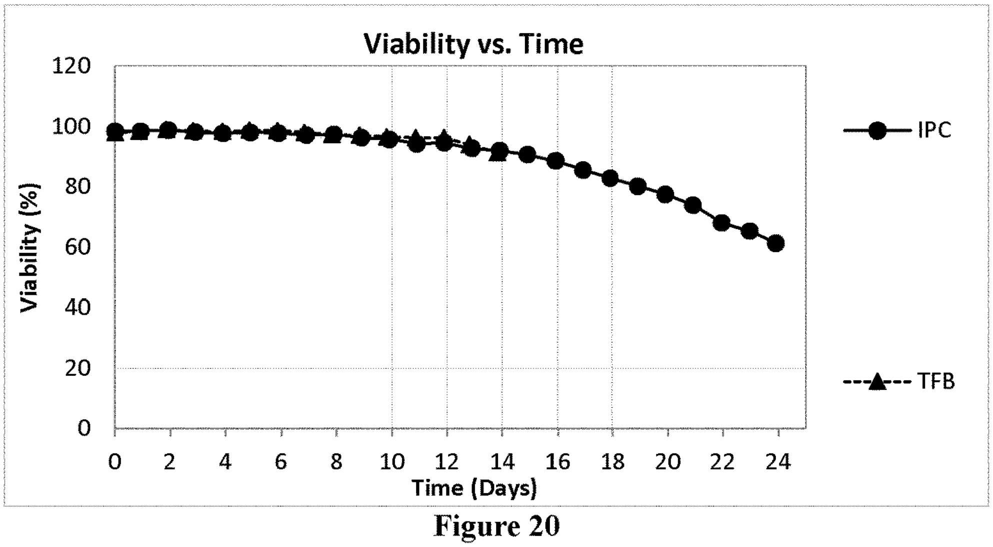
FIG. 20 shows the viability (%) plotted versus the process time (days) for processes A and B in Example 4.

FIG. 20 shows that process B can sustain a comparable cell viability with process A before day 14 at the same 3 L scale.

Figure 21:
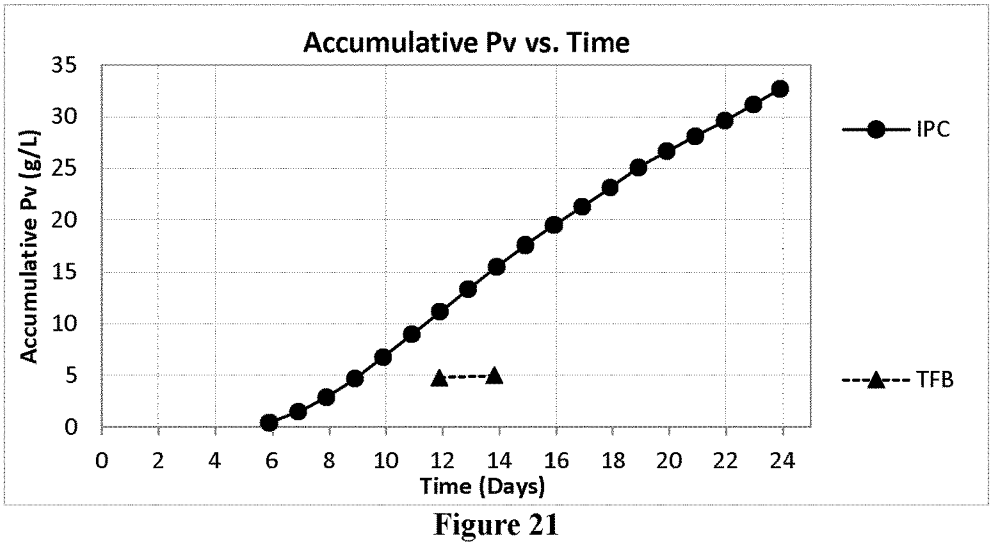
FIG. 21 shows the accumulative Pv (g/L) plotted versus the process time (days) for processes A and B in Example 4.

FIG. 21 shows that accumulative Pv from process B is approximately 6.56 times higher than the final concentration in the traditional fed-batch process A at the same 3 L scale.

Figure 22:
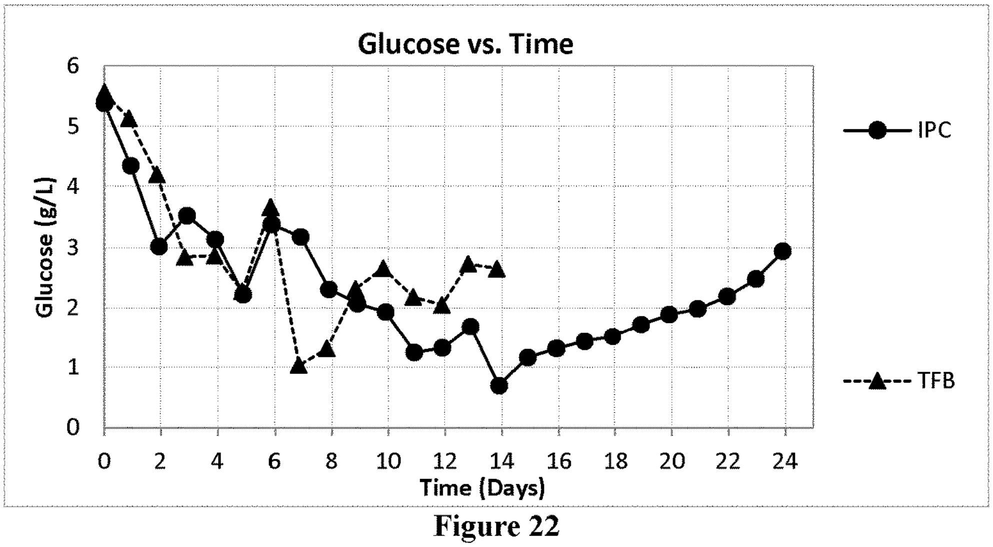
FIG. 22 shows the glucose concentration for processes A and B in Example 4.

FIG. 22 shows that glucose concentration control for process A and process B is comparable at the same 3 L scale.

Figure 23:
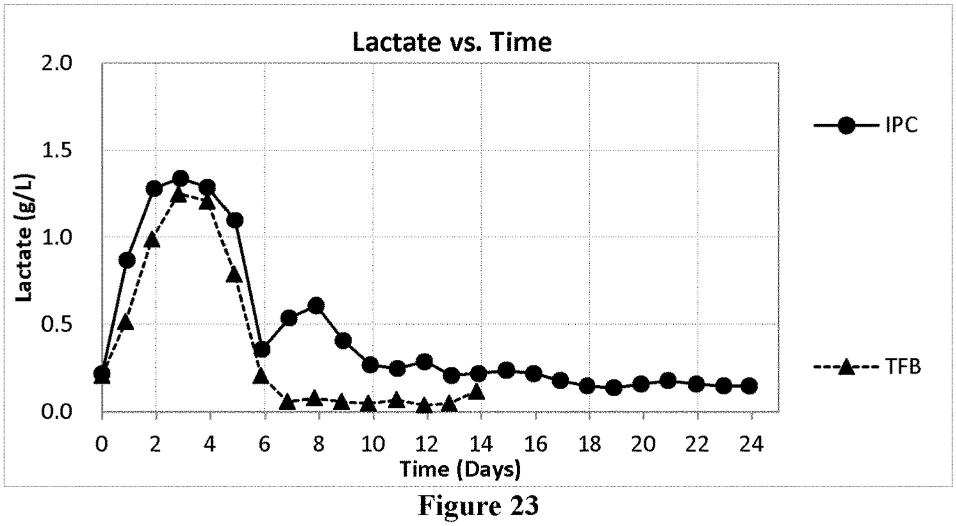
FIG. 23 shows the lactate concentration for processes A and B in Example 4.

FIG. 23 shows that a typical lactate production period during the exponential growth phase followed by the lactate consumption is observed in both process A and B at the same 3 L scale.

Figure 24:
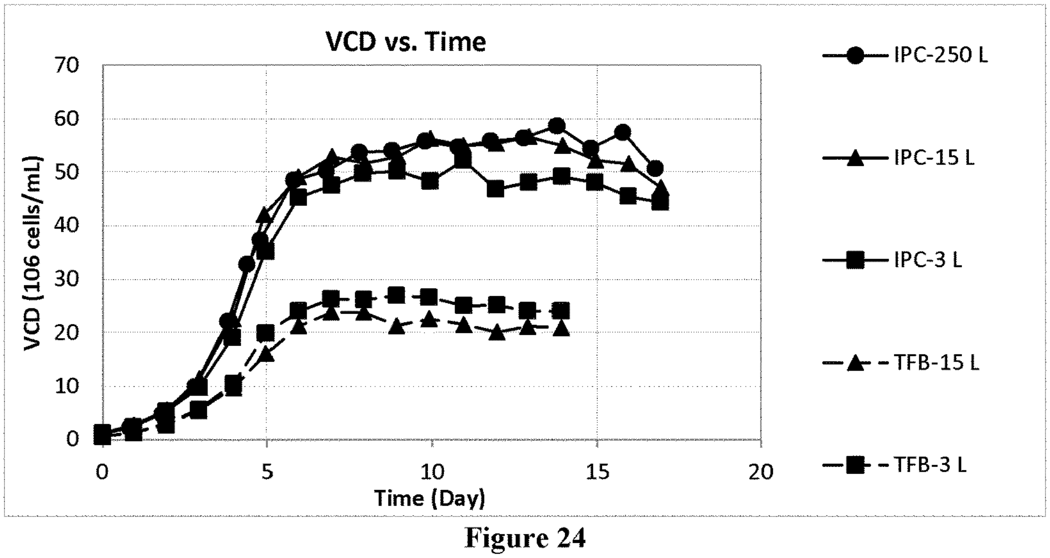
FIG. 24 shows the viable cell density ($10^6$/mL) plotted versus the process time (days) for process A (traditional Fed-batch) and process B (intensified perfusion culture) at different scales.

FIG. 24 shows that longer exponential growth phase and almost twice higher peak viable cell density are demonstrated in the process B when compared with the traditional fed-batch process A. The viable cell density results of process B when scaled up to 15 L and 250 L scale were comparable with the 3 L scale.

Figure 25:
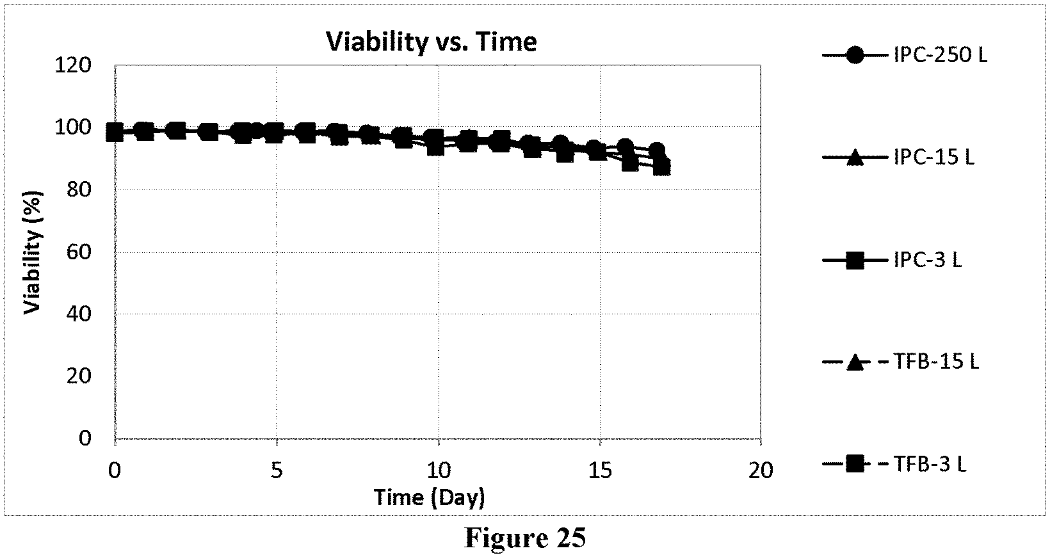
FIG. 25 shows the viability (%) plotted versus the process time (days) for process A (traditional Fed-batch) and process B (intensified perfusion culture) at different scales.

FIG. 25 shows that process B can sustain a comparable cell viability with process A. The viability results of process B when scaled up to 15 L and 250 L scale were comparable with the 3 L scale.

Figure 26:
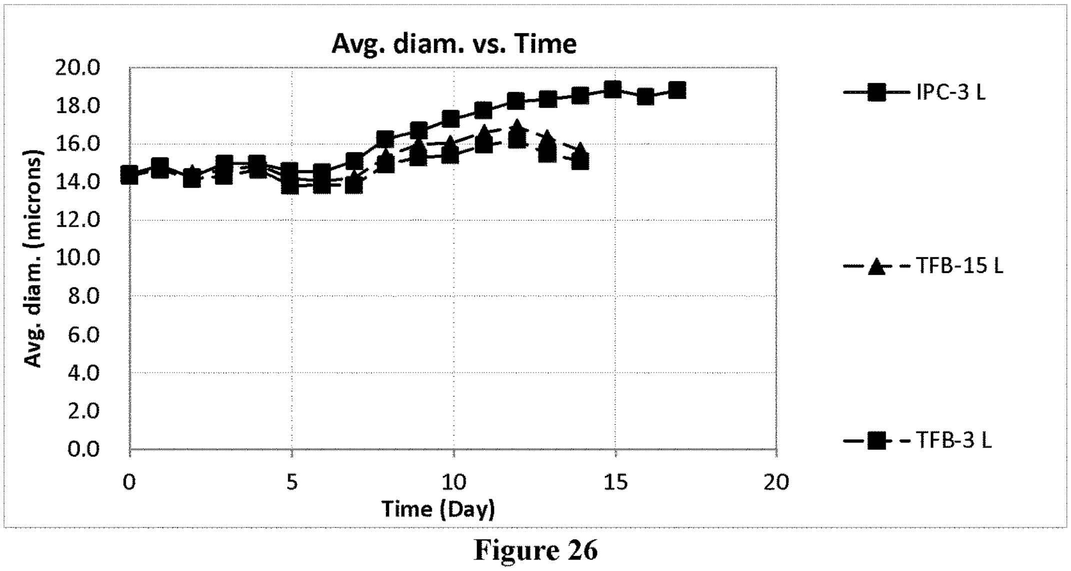
FIG. 26 shows the cell average diameter plotted versus the process time (days) for process A (traditional Fed-batch) and process B (intensified perfusion culture) at different scales.

FIG. 26 shows that the cell average diameter of process B was larger than that of traditional fed-batch process.

Figure 27:
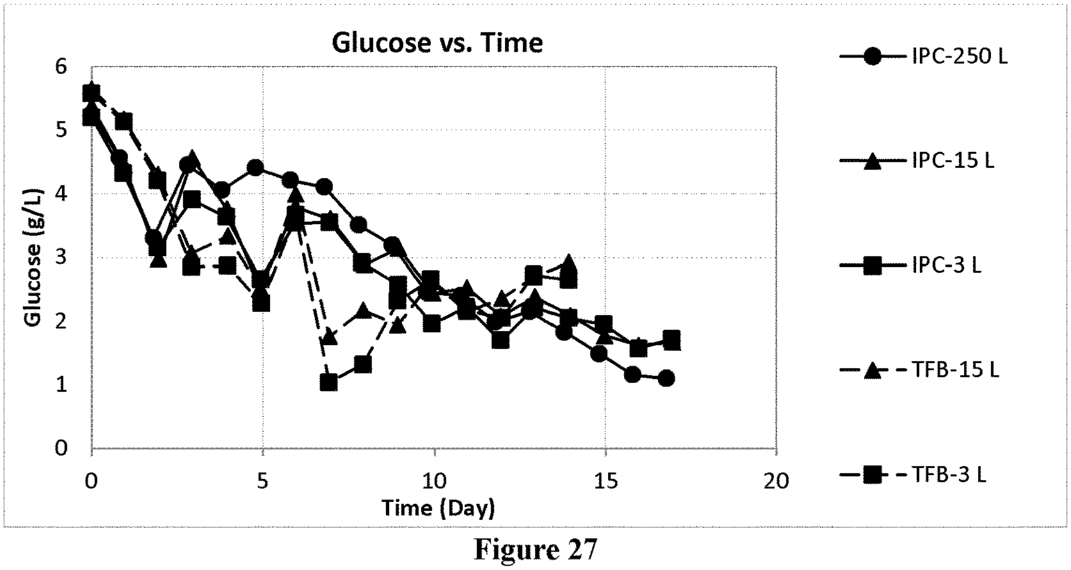
FIG. 27 shows the glucose concentration of culture plotted versus the process time (days) for process A (traditional Fed-batch) and process B (intensified perfusion culture) at different scales.

FIG. 27 shows that the glucose profiles differ between different processes because of different glucose control strategy.

Figure 28:
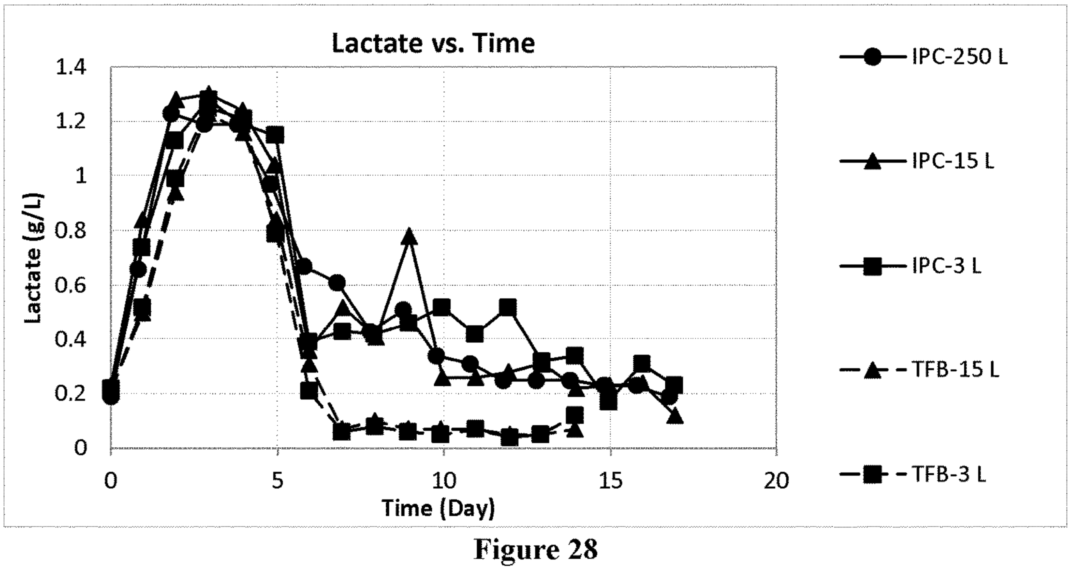
FIG. 28 shows the lactate concentration of culture plotted versus the process time (days) for process A (traditional Fed-batch) and process B (intensified perfusion culture) at different scales.

FIG. 28 shows that a typical lactate production period during the exponential growth phase followed by the lactate consumption is observed in both process A and process B.

Figure 29:
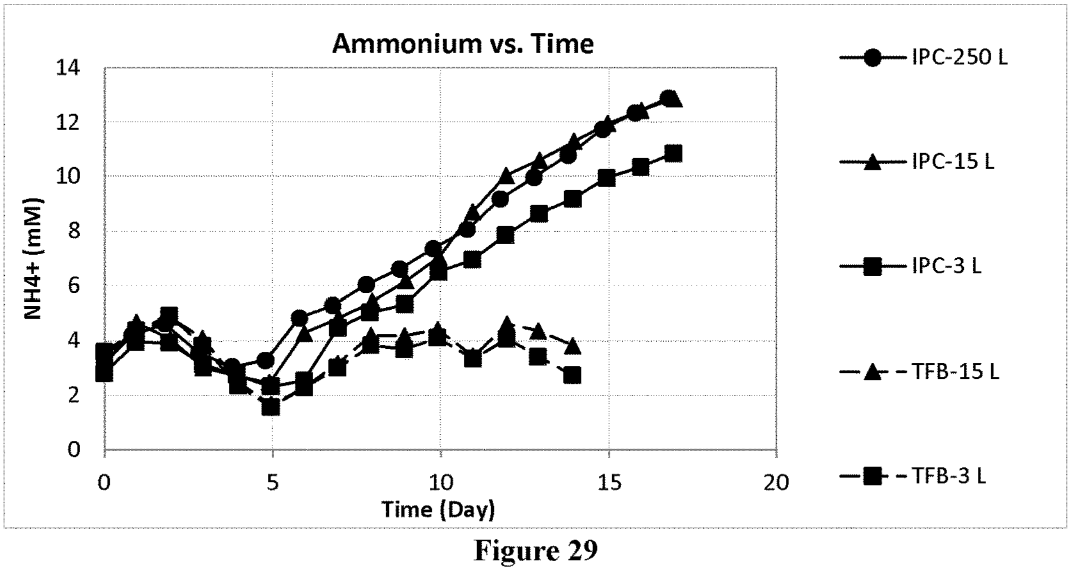
FIG. 29 shows the ammonium concentration of culture plotted versus the process time (days) for process A (traditional Fed-batch) and process B (intensified perfusion culture) at different scales.

FIG. 29 shows that the ammonium level of process B was higher than that of traditional fed-batch process.

Figure 30:
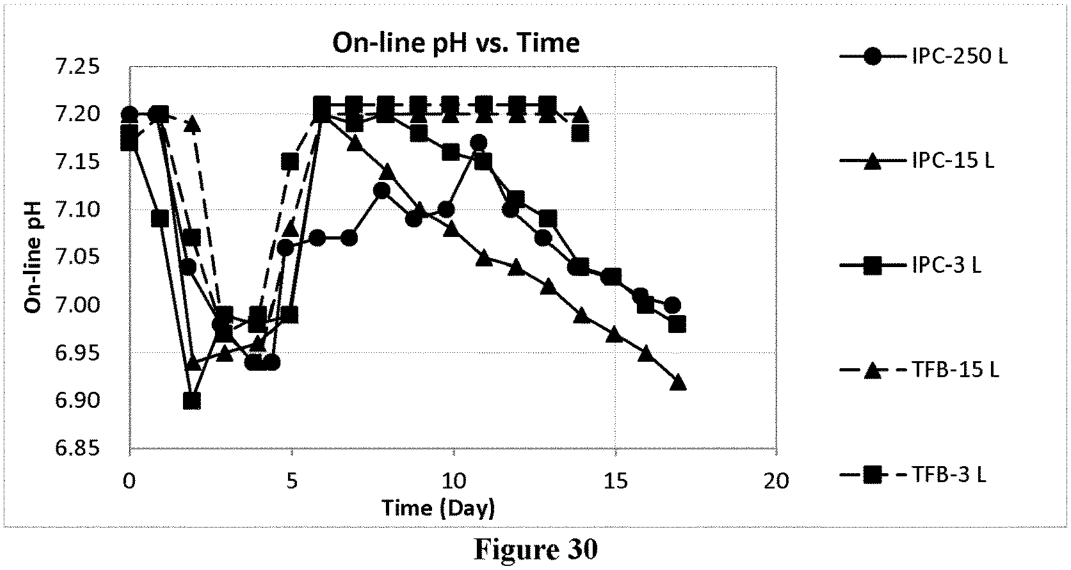
FIG. 30 shows the on-line pH of culture plotted versus the process time (days) for process A (traditional Fed-batch) and process B (intensified perfusion culture) at different scales.
Figure 31:
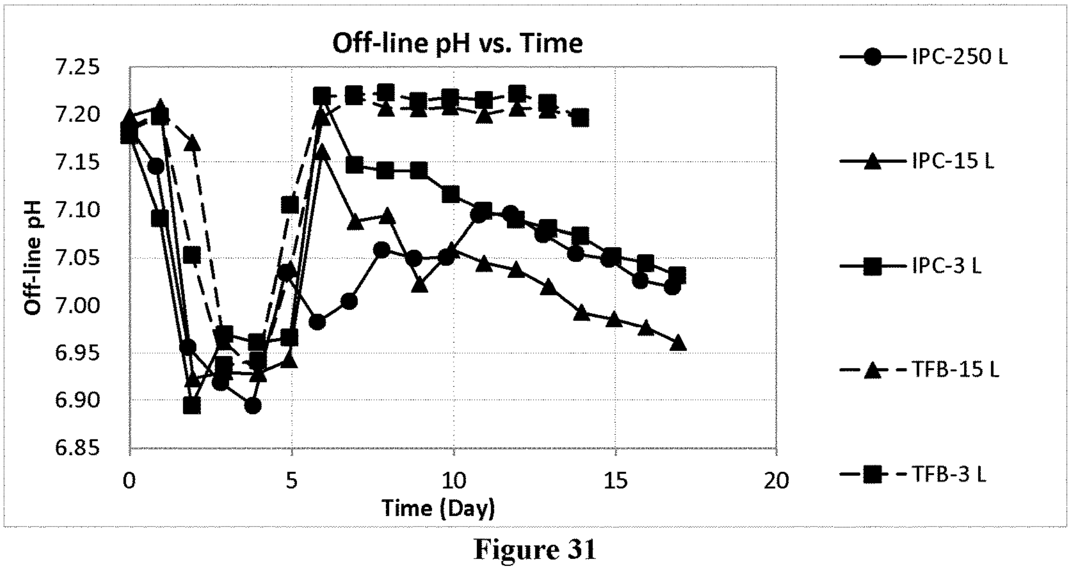
FIG. 31 shows the off-line pH of culture plotted versus the process time (days) for process A (traditional Fed-batch) and process B (intensified perfusion culture) at different scales.

FIGS. 30 and 31 show that pH was well controlled in both process A and process B, and the pH was slightly lower as the process scaled up.

Figure 32:
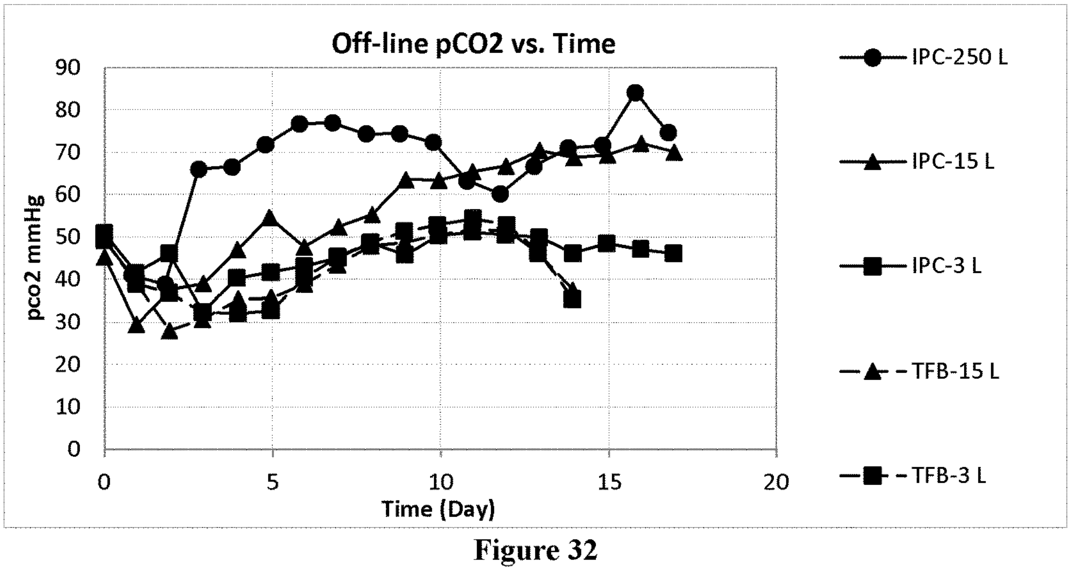
FIG. 32 shows the pCO2 level of culture plotted versus the process time (days) for process A (traditional Fed-batch) and process B (intensified perfusion culture) at different scales.

FIG. 32 shows that $pCO_2$ profile of process B was comparable with process A at the same scale. And the $pCO_2$ level increases as the process scaled up.

Figure 33:
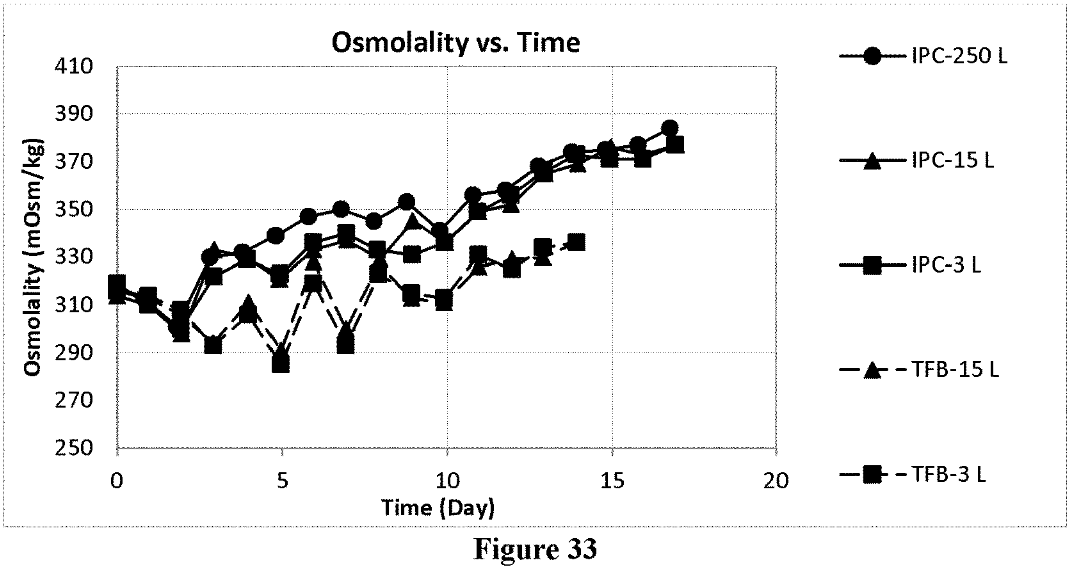
FIG. 33 shows the osmolality of culture plotted versus the process time (days) for process A (traditional Fed-batch) and process B (intensified perfusion culture) at different scales.

FIG. 33 shows that the osmolality of process B was slightly higher than process A, but it was well controlled under 400 mOsm/Kg.

Figure 34:
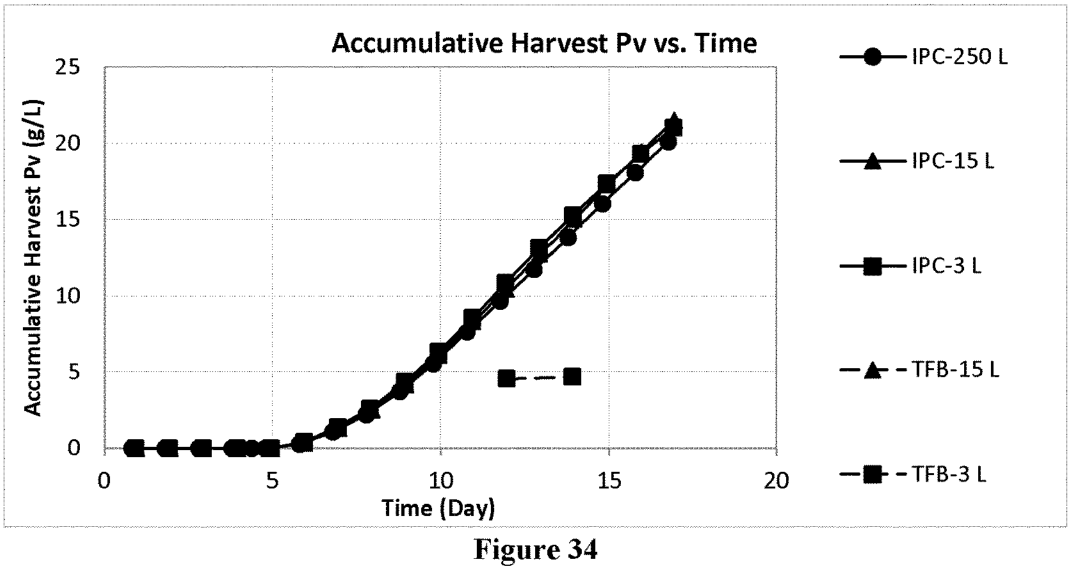
FIG. 34 shows the accumulative Pv (g/L) plotted versus the process time (days) for process A (traditional Fed-batch) and process B (intensified perfusion culture) at different scales.

FIG. 34 shows that accumulative Pv from process B is approximately 4.5 times higher than the final concentration in the traditional fed-batch process A. The accumulative Pv of process B at different scales all reached above 20 g/L.

Figure 35:
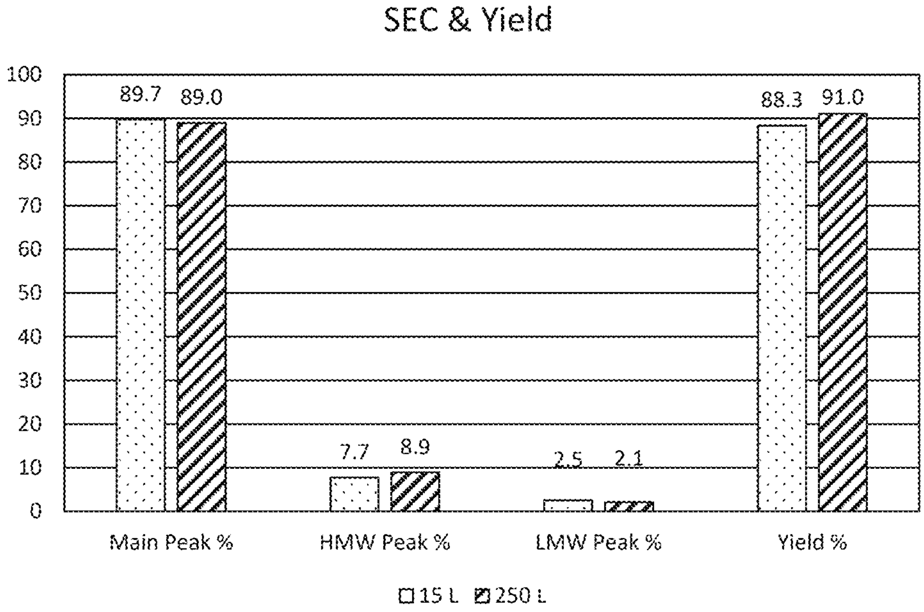
FIG. 35 shows the SEC results and yield of the capture step for process B (intensified perfusion culture) at 15 L and 250 L scales in Experiment 4.

FIG. 35 shows comparisons of the aggregates and fragments produced by the process B at 15 L scale and at 250 L scale. SEC main peaks from the process B at both scales are comparable.

Figure 36:
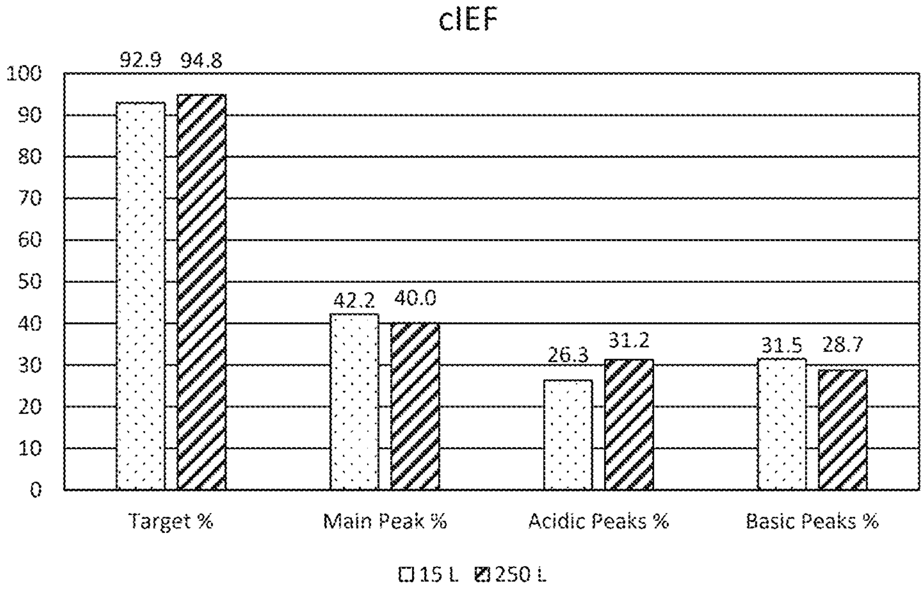
FIG. 36 shows the cIEF (Capillary Isoelectric Focusing) results for process B (intensified perfusion culture) at 15 L and 250 L scales in Experiment 4.

FIG. 36 shows cIEF main peaks along with reduction of the acidic peaks is achieved in process B compared with process A and process C.

Next, continuous process was evaluated for the direct product capture process of materials from intensified perfusion culture process B. The harvest material from the from process B was collected from Day 7 to Day 18, and stored in four bags for Day 7 to Day 10, Day 10 to Day 13, Day 13 to Day 16, and Day 16 to Day 18, respectively. The yield and productivity of continuous process was calculated, meanwhile the product quality attributes, SEC purity and HCP content, were also evaluated.

Continuous Direct Product Capture Process:

The continuous mode chromatography was performed on BioSMB PD system with three 1.1/5.0 cm (inner diameter/bed height) columns and BioSMB Process system with three 10.0/5.2 cm (inner diameter/bed height) columns at 15 L scale and 250 L scale, respectively. Both columns were packed with MABSELECT™ PRISM™ resin. In the load phase and post-load wash phase, two columns were connected in tandem, while in the other phases, only one single column was processed. These two flowpaths were processed in parallel on BioSMB system and switched among three columns automatically.

The loading capacity and residence time of continuous process were calculated based on the break through curves at different residence time and load concentration. The chromatography step was done at room temperature (18-26° C.). The yield was calculated based on the product amount in elution pool divided by the product amount in loading pool. The concentration of elution pool was determined by UV absorbance at 280 nm wavelength, while the concentration of loading pool was determined by Protein A HPLC. The load volume was determined by the volume totalizer of chromatography system, while the elution pool volume was determined by the net weight of collected sample. The productivity was calculated based on the processed product amount divided by the process time and the volume of resin.

The elution pool was neutralized to pH5.5, and then filtrated with 0.2 μm PES syringe filter after elution. The SEC purity and HCP content of the neutralized pool were determined by SEC HPLC and commercial ELISA kit for CHO cells, respectively. The yield and product quality attributes (including SEC purity, cIEF purity, and HCP content) of these two runs were summarized in Table 6. The consistent yield and product quality attributes data across culture time and scale reveals that the intensified perfusion culture process B is robust.

TABLE 5

Summary of Continuous Capture Process at 15 L Scale

| Harvest Time (Day) | Load Capacity (mg/mL resin) | SEC Purity (%) Monomer | HMW | LMW | HCP Content (ppm) | cIEF(%) Target | Basic Peaks | Main Peak | Acidic Peaks | Yield (%) |
|---|---|---|---|---|---|---|---|---|---|---|
| 7-10 | 38 | 88.1 | 8.9 | 3.0 | 559 | 89.9 | 26.5 | 47.1 | 26.3 | 88.3 |
| 10-13 | 47 | 88.9 | 8.3 | 2.8 | 597 | 91.9 | 24.7 | 39.3 | 35.9 | |
| | | 92.0 | 4.2 | 3.8 | 209 | 90.5 | 19.3 | 32.6 | 48.0 | |
| 13-16 | 48 | 90.2 | 7.8 | 2.0 | 722 | 94.7 | 28.1 | 43.3 | 28.6 | |
| 16-17 | 44 | 89.9 | 7.9 | 2.2 | 885 | 94.7 | 28.2 | 44.0 | 27.9 | |

TABLE 6

Summary of Continuous Capture Process at 250 L Scale

| Harvest Time (Day) | Load Capacity (mg/mL resin) | SEC Purity (%) Monomer | HMW | LMW | HCP Content (ppm) | cIEF(%) Target | Basic Peaks | Main Peak | Acidic Peaks | Yield (%) |
|---|---|---|---|---|---|---|---|---|---|---|
| 7 | 37 | 81.8 | 15.5 | 2.7 | 510 | 90.5 | 35.5 | 43.0 | 21.5 | 91.0 |
| 8 | 41 | 83.1 | 14.1 | 2.8 | 580 | 91.0 | 33.3 | 42.4 | 24.3 | |
| 9 | 37 | 86.0 | 11.6 | 2.4 | 753 | 91.8 | 32.2 | 40.0 | 27.8 | |
| 10 | 43 | 88.5 | 9.3 | 2.2 | 712 | 93.1 | 30.8 | 39.8 | 29.3 | |
| 11 | 46 | 89.3 | 8.7 | 2.1 | 756 | 94.8 | 31.2 | 40.3 | 28.5 | |
| 12 | 46 | 89.9 | 8.3 | 1.9 | 721 | 95.2 | 30.8 | 40.6 | 28.6 | |
| 13 | 44 | 90.3 | 7.7 | 2.0 | 698 | 96.1 | 29.4 | 39.3 | 31.3 | |
| 14 | 47 | 90.9 | 7.0 | 2.0 | 729 | 96.1 | 30.6 | 38.9 | 30.5 | |
| 15 | 47 | 90.5 | 7.4 | 2.1 | 710 | 96.3 | 30.5 | 39.2 | 30.3 | |
| 16 | 45 | 90.6 | 7.5 | 2.0 | 719 | 96.3 | 30.7 | 39.7 | 29.6 | |
| 17 | 44 | 89.7 | 8.3 | 2.0 | 841 | 96.6 | 32.1 | 40.3 | 27.7 | |

We claim:

1. A method for producing a biological substance comprising:

(a) culturing a cell culture comprising Chinese Hamster Ovary (CHO) cells and a cell culture medium for culturing the CHO cells, wherein the CHO cells are cultured at a range of about 35° C. to about 37° C., and the cell culture is established by inoculating at about 0.6-0.8×$10^6$ viable cells/mL, (b) perfusing the cell culture in a bioreactor with a basal medium and a feed medium, and (c) harvesting the biological substance, wherein the basal medium and the feed medium are fed to the cell culture at different rates, the cell culture is continuously passed through a separation system to harvest the biological substance from the bioreactor, and the cells are retained in the bioreactor without bleeding, wherein the basal medium is perfused at a perfusion rate of about 0.3 to about 0.6 working volume per day (VVD) from the first day and the perfusion rate is increased to about 1.5 to about 2.0 VVD between days 4-5 of the culturing, wherein the perfusion of the feed medium is started one day after the perfusion rate of the basal medium is increased and is started at a rate ranging from about 1 to 5% of the perfusion rate of the basal medium, then increased to about 7 to 9% between days 12-13 of the culturing and maintained at about 6 to 7% from days 18-19 of the culturing, and wherein the method further comprises subjecting the cell culture to a temperature shift to a temperature in the range of about 32° C. to about 33° C. in response to a predetermined peak viable cell density (VCD), wherein the feed medium is a CHO cell culture medium or a combination of CHO cell culture media.

2. The method of claim 1, wherein the separation system is an alternating tangential flow (ATF) device or tangential flow filtration (TFF) device.

3. The method of claim 1, wherein the separation system comprises a hollow fiber filter, wherein the pore size of the hollow fiber filter is about 0.08 mm to about 0.5 mm.

4. The method of claim 3, wherein the pore size of the hollow fiber filter is about 0.1 μm to about 0.5 μm.

5. The method of claim 3, wherein the pore size is about 0.2 μm or about 0.45 μm.

6. The method of claim 1, wherein an antifoam is added to the bioreactor.

7. The method of claim 1, wherein a microsparger is used.

8. The method of claim 7, wherein the microsparger delivers oxygen at a flow rate in a range of about 0.2 to about 0.5 volume of gas per volume of liquid per minute (VVM).

9. The method of claim 1, wherein the biological substance is chosen from receptors, enzymes, fusion proteins, blood proteins, multifunctional proteins, viral or bacterial proteins, and immunoglobulins.

10. The method of claim 1, wherein said method achieves an accumulative volumetric productivity (Pv) of about 10 g/L or more.

11. The method of claim 1, wherein said method achieves an accumulative volumetric productivity (Pv) of about 15 g/L or more.

12. The method of claim 1, wherein said method achieves an accumulative volumetric productivity (Pv) of about 20 g/L or more.

13. The method of claim 1, further comprising subjecting the harvested biological substance to a continuous product capture process by at least one chromatography step.

14. The method of claim 1, wherein the basal medium is a CHO cell culture medium.

* * * * *